United States Patent [19]
Greenberg et al.

[11] Patent Number: 5,743,916
[45] Date of Patent: Apr. 28, 1998

[54] DRILL GUIDE WITH REMOVABLE FERRULES

[75] Inventors: Alex M. Greenberg; Douglas M. Spranger; Paul J. Mulhauser, all of New York, N.Y.

[73] Assignee: Human Factors Industrial Design, Inc., New York, N.Y.

[21] Appl. No.: 382,235

[22] Filed: Jan. 31, 1995

Related U.S. Application Data

[63] Continuation-in-part of Ser. No. 300,707, Sep. 2, 1994, which is a continuation-in-part of Ser. No. 919,783, Jul. 24, 1992, Pat. No. 5,409,493, which is a continuation-in-part of Ser. No. 719,178, Jun. 21, 1991, Pat. No. 5,133,720, which is a continuation-in-part of Ser. No. 552,703, Jul. 13, 1990, Pat. No. 5,026,376.

[51] Int. Cl.⁶ .................................................. A61B 17/58
[52] U.S. Cl. ........................... 606/102; 606/96; 606/172
[58] Field of Search .................... 606/96, 98, 80, 606/102, 180, 172, 100, 104, 105, 86, 87, 79, 72, 53

[56] References Cited

U.S. PATENT DOCUMENTS

| | | | |
|---|---|---|---|
| 4,119,092 | 10/1978 | Gil | 606/105 |
| 4,142,517 | 3/1979 | Stavropoulos | 606/79 |
| 4,341,206 | 7/1982 | Perrett | 606/102 |
| 4,710,075 | 12/1987 | Davison | 606/80 |
| 4,788,970 | 12/1988 | Kara | 606/96 |
| 5,047,034 | 9/1991 | Sohngen | 606/87 |
| 5,152,792 | 10/1992 | Watkins | 606/87 |
| 5,192,293 | 3/1993 | Cartwright | 606/96 |
| 5,403,322 | 4/1995 | Herzenberg | 606/98 |

*Primary Examiner*—Sam Rimell
*Assistant Examiner*—Luke Yeh
*Attorney, Agent, or Firm*—Meltzer, Lippe, Goldstein et al.

[57] ABSTRACT

A drill guide is disclosed including a sleeve mounted on a handle. The sleeve of the drill guide has a bore which is dimensioned for slidably receiving a bit sizing ferrule therein. The bit sizing ferrule has a sized bore for demountably inserting a drill bit or other instrument therein having a particular width.

20 Claims, 24 Drawing Sheets

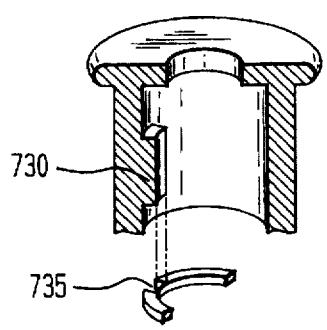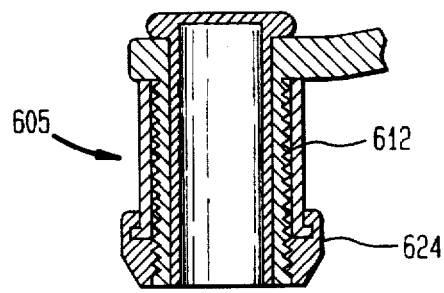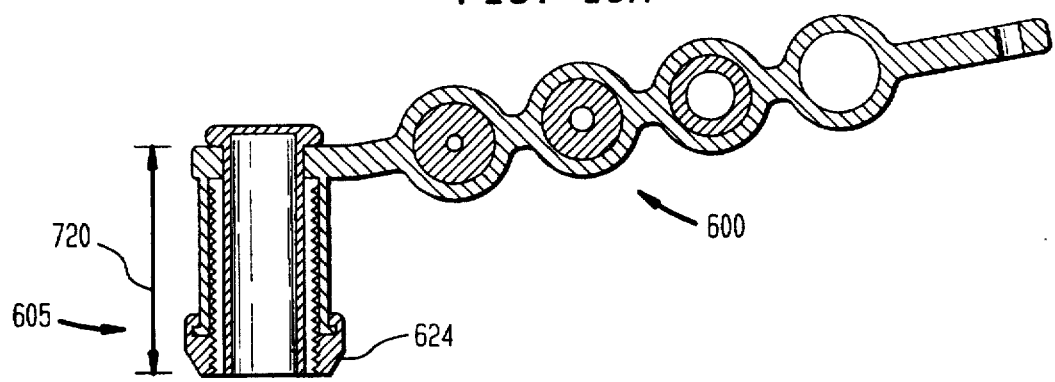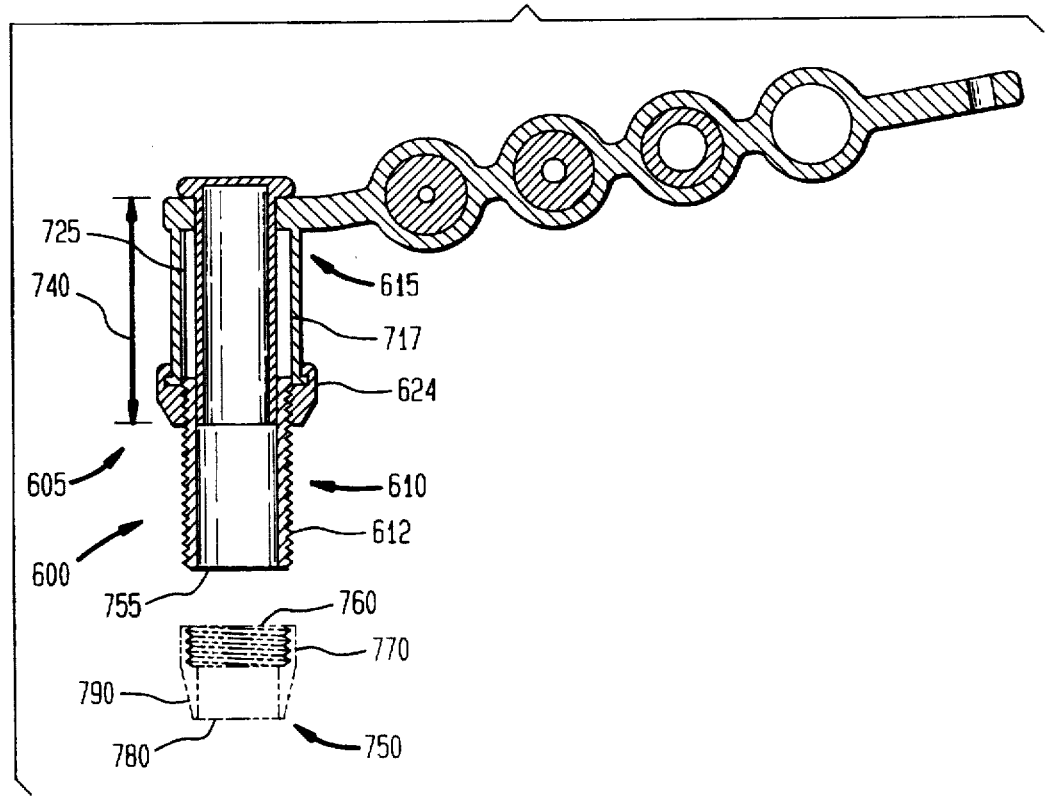

DRILL GUIDE WITH REMOVABLE FERRULES

RELATED APPLICATIONS

This is a continuation-in-part of U.S. patent application Ser. No. 08/300,707 entitled "Single-Handed Surgical Drill Depth Guide With Mandibular Retractor", filed Sep. 2, 1994 for Alex Greenberg which is a continuation-in-part of U.S. patent application Ser. No. 07/919,783 entitled "Single-Handed Surgical Drill Depth Guide", filed Jul. 24, 1992 now U.S. Pat. No. 5,409,493 for Alex Greenberg which is a continuation-in-part of application Ser. No. 07/719,178, filed Jun. 21, 1991 now U.S. Pat. No. 5,133,720, which is a continuation-in-part of application Ser. No. 07/552,703, filed Jul. 13, 1990 now U.S. Pat. No. 5,026,376.

Furthermore, the following additional applications are commonly owned and contain subject matter related to the present application:

1. U.S. application Ser. No. 08/300,708 now U.S. Pat. No. 5,558,622 entitled "Mandibular Border Retractor And Method For Fixating a Fractured Mandible", filed for Alex Greenberg on Sep. 2, 1994.

2. U.S. application Ser. No. 08/314,600 now U.S. Pat. No. 5,599,185 entitled "An Improved Dental Implant Healing Abutment" filed for Alex Greenberg on Sep. 28, 1994.

The contents of these applications and patents are incorporated herein by reference.

FIELD OF THE INVENTION

The present invention relates to a drill guide with removable ferrules. The inventive drill guide can be used to drill into many different types of material such as bone, wood, metal, plastic and glass. More particularly, the invention relates to a drill guide for guiding bits having a variety of widths in precision drilling, such as in the surgical drilling of anatomical bones (e.g., cranial, mid-facial or mandibular bones) exposed by an incision. The inventive device is particularly useful for the treatment of bone fractures in cranio-maxillofacial regions or any other anatomical bone structure, and controlling depths of holes drilled into various materials, such as wood, plastic, metal or concrete, using hand held consumer or industrial drilling tools.

BACKGROUND OF THE INVENTION

It is often desirable to drill holes of a precise length and width or to use countersinking drill bits to widen an inlet of a hole. In addition, to fasten two pieces of material together, it is necessary to drill a hole in each material. The two holes must be properly aligned and may have different widths. For example, to attach two pieces of wood used in making furniture or cabinets, a narrow hole in one piece of wood is a traction hole which receives and holds a screw. In the other piece of wood, a wider hole is drilled which is a gliding hole for slidably receiving the screw therethrough. Similar precisely sized, aligned and centered holes are needed to be drilled in many material, such as cements and plastics. Precision drilling is also very common during surgery or during treatment of bones fractures in the medical field.

For example, the treatment of bone fractures in the cranio-maxillofacial region generally proceeds by reducing the fractured bones to their anatomically correct positions, and thereafter fixing the bones in place. The bones may be fixed in place either by interosseous wiring, or by the technique of miniplate osteosynthesis. In either case, holes must be drilled in the bone structure for receiving the interosseous wire or screws for holding the miniplates to the bone.

In the drilling of holes into the bone structure, great care must be taken to ensure that the holes are drilled at precisely the correct position and to precisely the correct depth. If the holes are not drilled at the correct location, strain may be transmitted by screws to the surrounding bone structure. This may cause the bone to resorb in the vicinity of the screws resulting in loosening of the hardware.

Similarly, complications, such as blindness, extraocular muscle dysfunction, retinal or corneal damage, and severe tissue trauma could result if the depth of holes is not gauged accurately when drilling orbital bones. Accordingly, it is desirable during the drilling procedure to use an instrument which will prevent the operator from drilling too deeply into bones of cranio-maxillofacial regions. Furthermore, it is also desirable to center and align the drill bit to better control the angle of the drilling. This permits greater flexibility in the placement of implants. For example, if screws are to be placed into the frontal bone, superior to the zygomaticofrontal suture, they are preferably inserted at a downward slanting angle with respect to the forehead. This ensures that neither the screws nor the drill bit enters the anterior cranial fossa. See M. Zide, "The Placement of Screws Above the Zygomaticofrontal Suture," 48 J. Oral & Maxillofacial Surg. 813–816 (1990).

Drilling into the mandibular bone is also required for many surgical procedures such as procedures requiring implantation of various devices. One example that requires such drilling is shown in a brochure for The Bosker Transmandibular Implant (TMI) Reconstruction System, by the Walter Lorenz Surgical Instruments, Inc. of Jacksonville, Fla. The Bosker TMI uses a template with a preset drill guide. Therefore, adjustable drill guides cannot be used.

A prior art drill guide for controlling the angle and the depth of a hole drilled into anatomical bone, is disclosed in a catalog published in 1992 by Synthes Maxillofacial, a surgical supply company located in Paoli, Pa. This drill guide 1 is depicted in FIG. 1. The drill guide 1 has a threaded inner sleeve 2 which is screwed into a first opening 4a of an outer sleeve 4. By rotating the inner sleeve 2 with respect to the outer sleeve 4, the inner sleeve 2 may be extended from, or retracted into, the outer sleeve 4. A knurled nut 3 is provided which may be loosened to permit the rotation of the inner sleeve 2. After the inner sleeve 2 is adjusted to a desired length from the outer sleeve 4, the knurled nut 3 may be tightened to prevent rotation of the inner sleeve 2.

The outer sleeve 4 is attached to, and integral with, a handle 5. The outer sleeve 4 and handle 5 are connected so as to form an obtuse angle. Such a drill guide 1 is useful in a variety of surgical operations. For example, the use of the drill guide in an exemplary surgical operation is illustrated in FIGS. 2–3 and proceeds as follows. An incision is made in the region of the fracture, the skin is retracted, and the bones are reduced to their correct anatomical positions. One or more threaded guide wires W are then inserted into the bones B having a fracture F, as depicted in FIG. 2, using a small diameter drill guide 1. The depth to which the guide wire W is inserted into the bones B is then measured by sliding a depth gauge sleeve 8 (FIG. 1) over the exposed portion of the guide wire W.

Knowing the depth of penetration of the guide wire W, the drill guide 1 may be adjusted so as to limit the drilling of a hole to a desired depth. A cannulated drill bit 6 (i.e., a drill bit with a central bore) is inserted into a distal end 4b of the outer sleeve 4 until the quick coupling 7 of the drill abuts against the distal end 4b of the outer sleeve 4 as depicted in FIG. 1. While the drill guide 1 is held in this position with one hand, the depth gauge sleeve 8 is inserted over the exposed portion of the drill bit 6a. Using the other hand, the knurled nut 3 is loosened, and the inner sleeve 2 rotated until the length of the exposed portion of the drill bit 6a equals the desired drilling depth. The knurled nut 3 is then tightened so that the inner sleeve 2 does not retract into, or extend from, the outer sleeve 4 during the drilling of the hole.

The adjusted drill guide 1 may then be inserted over the guide wire W until the inner sleeve 2 contacts the bone B, as depicted in FIG. 3. The cannulated drill bit 6 is inserted into the distal end 4b of the outer sleeve 4 of the drill guide 1 over the guide wire W. The drill is then operated to drill into the bones B until the quick coupling 7 of the drill abuts against the distal end 4b of the outer sleeve 4. Thus, the drill guide 1 acts as a stop, preventing the drilling of holes deeper than the length of the exposed portion of the drill bit 6a which protrudes from the drill guide 1 when the quick coupling 7 abuts against the distal end 4b of the outer sleeve 4.

This process is repeated using different size drill bits until a hole of desired width and depth is drilled. After the hole is drilled to the correct depth, a surgical screw is inserted into the hole and the guide wire is removed. The screws can also secure an implant, such as a miniplate, to the bone structure. The miniplate holds the bone structure together so that it can heal.

The prior art drill guides, while useful, are not entirely satisfactory for their above-described procedures. The prior art drill guides do not provide a single drill guide for aligning and centering drill bits of different thickness. Rather, according to the prior art, a different drill guide with a different width bore must be provided for each different width drill bit used in the operation. This is both inefficient and time consuming because many different size drill guides must be readily available in a sterilized condition.

Accordingly, it is an object of the present invention to overcome the disadvantages of the prior art.

SUMMARY OF THE INVENTION

The present invention achieves these and other objects by providing a drill guide. The drill guide has a handle and a sleeve having a first end attached to one end of the handle. The sleeve has a bore which is dimensioned for demountably inserting a ferrule into one end of the sleeve. The ferrule has a second bore dimensioned to receive therethrough an instrument having a particular width.

In an illustrative embodiment, the drill guide is a surgical drill guide which has many ferrules stored in compartments located within the handle. The second bore of each ferrule has a different width for receiving, and guiding, an instrument of a corresponding width. Each compartment on the handle illustratively has an opening on one end for receiving one of the ferrules, and another end having a snap-on device for snapping into the ferrule in order to retain it within the compartment.

Illustratively, each ferrule comprises a tube and a lip protruding from an outer surface of a first end of the tube. A second end of the tube is inserted into one end of the sleeve until the lip rests on that one end of the sleeve.

In yet another embodiment, a pair of the ferrules are adapted to attach together so as to protrude from the sleeve when inserted into the first bore of the sleeve. The exposed end of the attached pair of ferrules, which protrudes from the sleeve, has markings on its outer surface to indicate the depth of the drill bit or other instrument inserted through the second bore.

Illustratively, the drill guide also controls the depth of penetration into the bone of the drill bit or instrument inserted through the sleeve. This can be achieved in a number of ways. For instance, the drill guide sleeve may be a two-piece adjustable length sleeve with an inner segment connected to an outer segment. The inner segment adjustably retracts into, or extends from, the outer segment to adjust the length of the adjustable length sleeve. When a drill bit is fully inserted into one end of the sleeve (until, for example, a coupling abuts that end of the sleeve), a particular length of drill bit is exposed at the other end of the sleeve which exposed length depends on the adjusted length of the sleeve. Only the exposed length of drill bit may penetrate into the bone. Alternatively, the sleeve of the drill guide is a single piece sleeve. However, the ferrules themselves may be adjustably extended from or retracted into one end of the sleeve to adjust the exposed length of the drill bit which may penetrate into the bone.

In a further embodiment, a drill is provided, which has a head into which a drill bit is inserted. A sleeve is attached to the head so that the center of the bore of the sleeve is axially aligned with the drill bit (which is inserted therethrough). Illustratively, the sleeve length is manually or mechanically adjustable to control the drilling depth. Alternatively, or additionally, the sleeve bore is dimensioned for receiving a depth gauging ferrule for measuring the penetration depth of the bit.

In short, a drill guide, a drill and a precision drilling method using the inventive drill guide or drill are disclosed. The drill guide and drill are provided with removable ferrules wherein each ferrule has a particular width bore for aligning and guiding an instrument or drill bit having a corresponding width. Such a drill guide and a drill simplify precision drilling procedures.

BRIEF DESCRIPTION OF THE DRAWING

FIG. 10a illustrates a cross-sectional view of the drill guide of FIG. 9 in a retracted position.

FIG. 10b illustrates a cross-sectional view of the drill guide of FIG. 9 in a fully extended position.

FIG. 10c illustrates a cross-sectional view of the drill guide of FIG. 9 detailing a key and keyway mechanism.

FIG. 11 illustrates a cross-sectional view of the sleeve of the drill guide of FIG. 10a in greater detail.

FIG. 12b illustrates a top view of the drill guide of FIG. 12a.

FIG. 15b illustrates a back view of the embodiment shown in FIG. 15a.

FIG. 15c illustrates in greater detail a cross-sectional view of an appendage and a retaining body used in the embodiment shown in FIG. 15a.

FIG. 16b illustrates in greater detail a cross-sectional view of different retaining mechanisms used in the embodiment shown in FIG. 16a.

DETAILED DESCRIPTION OF THE INVENTION

Figure 1:
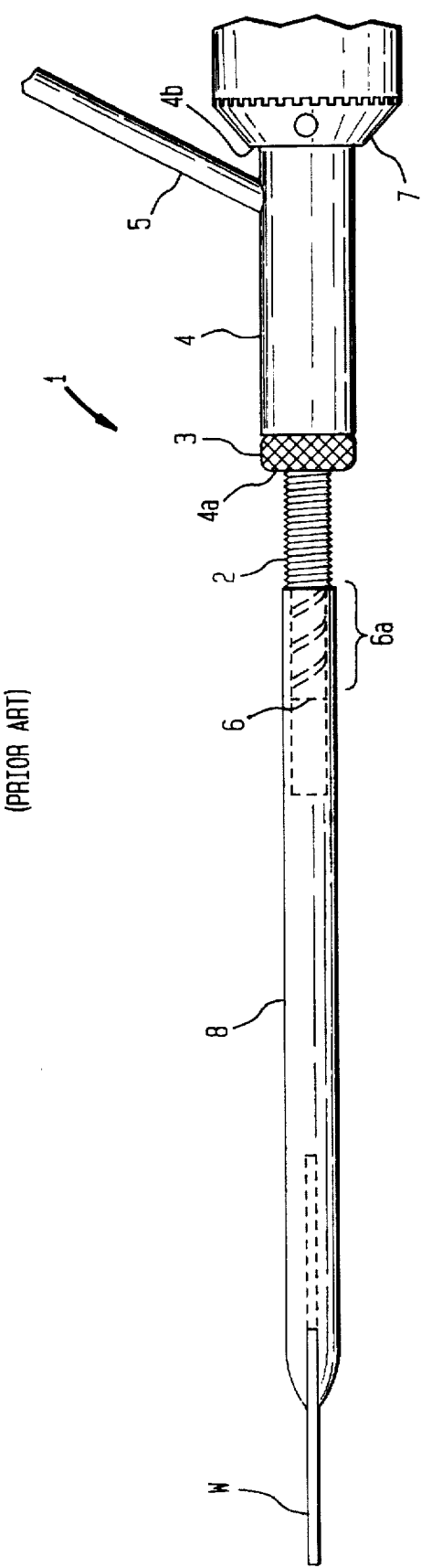
FIG. 1 illustrates a prior art drill guide.
Figure 2:
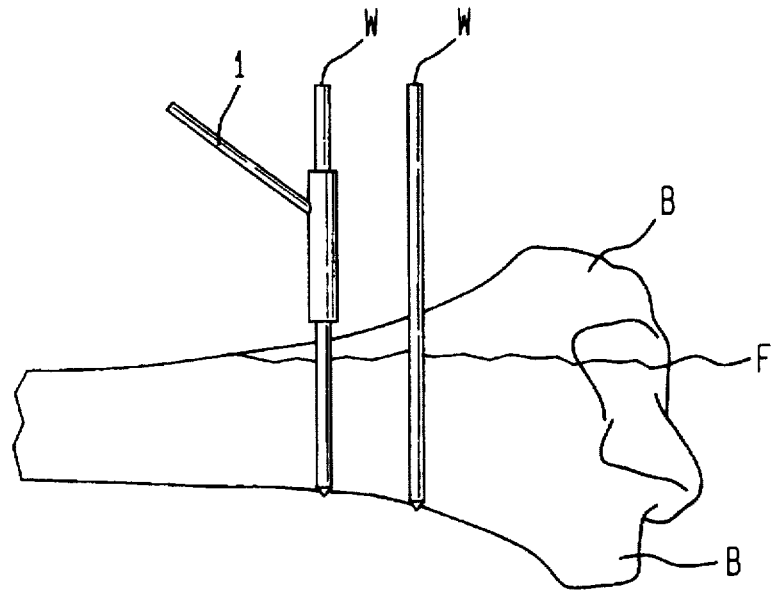
FIGS. 2-3 illustrate a surgical procedure for drilling holes into bone with the prior art drill guide of FIG. 1.
Figure 3:
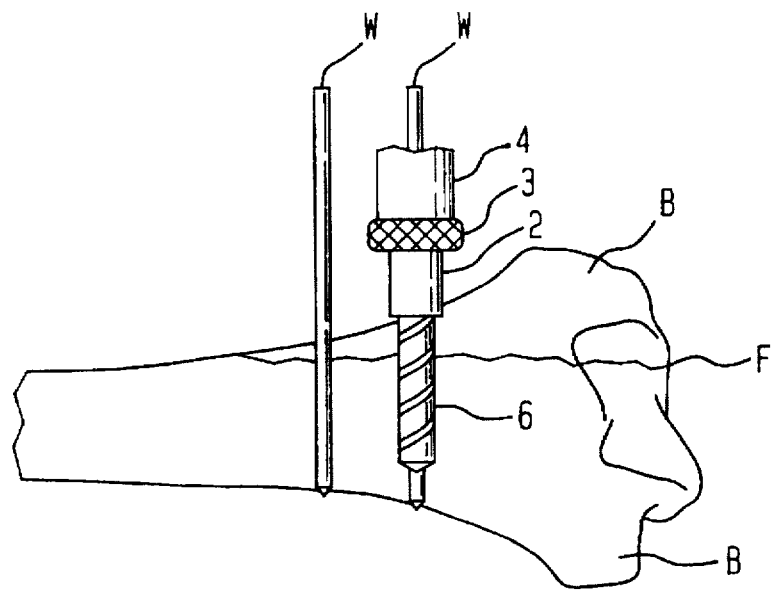
Figure 4A:
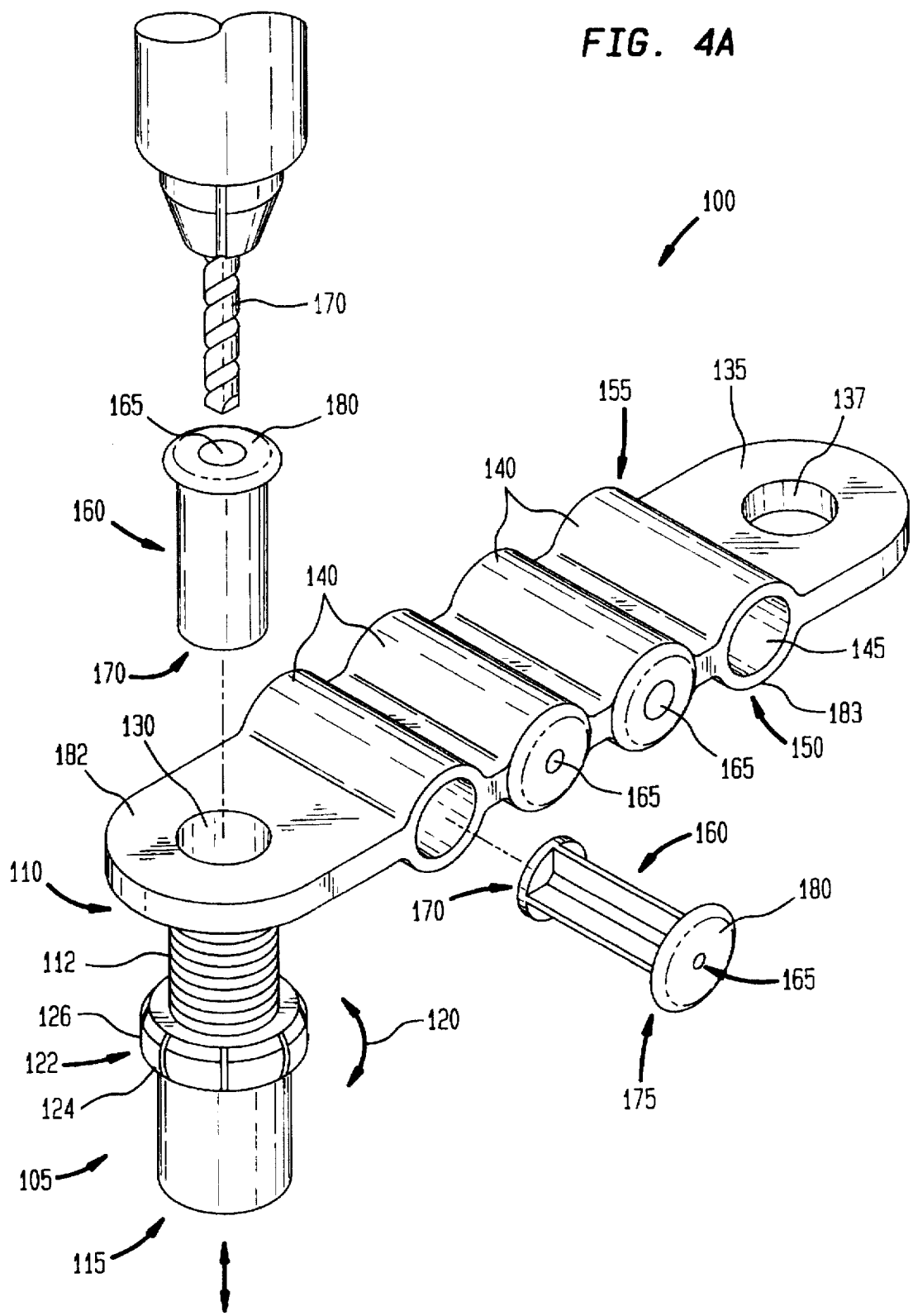
FIG. 4a illustrates a side elevation view of one embodiment of the drill guide with removable ferrules according to the invention.

A drill guide with removable ferrules 100 according to one embodiment of the present invention is depicted in FIG. 4a. The drill guide 100 has an adjustable length sleeve 105 which includes an inner telescopic segment 110 with threaded outer walls 112 and an outer telescopic segment 115 with threaded inner walls 117 (FIG. 5b).

The sleeve 105 has an adjustable length bore 130 which passes through both segments 110 and 115. The adjustable length bore 130 is designed to receive a bit sizing ferrule adapter therethrough.

As depicted, a handle 135 is connected to the inner segment 110. Illustratively, the handle 135 has a hole 137 which enables the drill guide 100 to be stored by hanging it on a hook, or suspending it from a cord or a chain. The handle 135 is shaped to have many cylindrical shaped containers 140. Each cylindrical shaped container 140 has a compartment 145 beginning from an open end 150 of the containers 140 and terminating by a closed end 155 located opposite the open end 150. The compartment 145 receives a bit sizing adapter 160 for storing within the cylindrical container 140.

The bit sizing ferrule adapter 160 has a body adapted to fit in the adjustable bore 130 and compartment 145. Each bit sizing adapter 160 has a sized bore 165 of a particular diameter for receiving a particular drill bit 170 having a specific diameter.

Figure 4B:
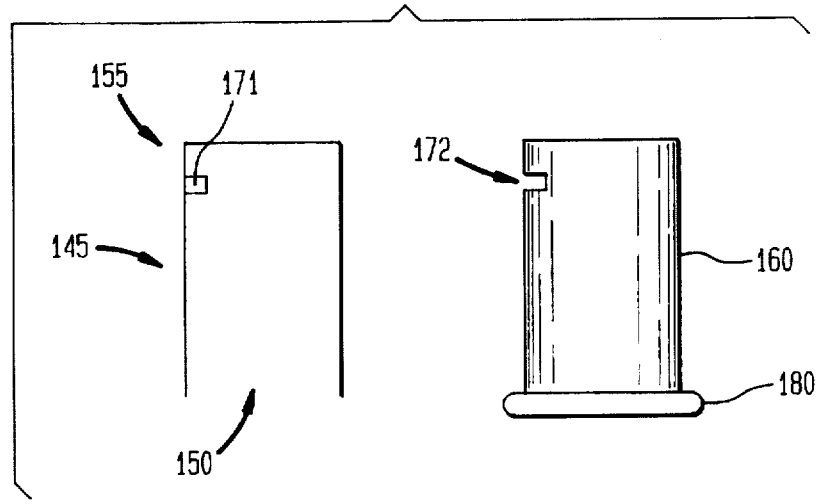
FIG. 4b illustrates a side elevation view of one embodiment of a storage compartment and a ferrule.
Figure 4C:
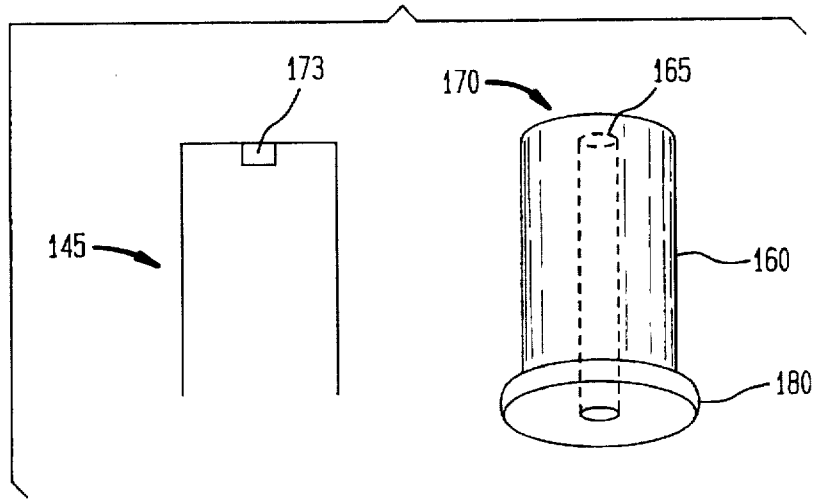
FIG. 4c illustrates a side elevation view of another embodiment of a storage compartment and a ferrule.

Mounted within the compartment 145, on the closed end 155 of the cylindrical container 140 is a mechanism for retaining the ferrule adapter 160 while stored within the compartment 145. Illustratively, as shown in FIG. 4b, the mechanism for retaining is a snap-on device with a protrusion 171 at the inner side of the compartment 145 that mates tightly with a depression 172 at the side of the ferrule adapter 160. This prevents the ferrule adapter 160 from falling out of the compartment 145 of the cylindrical container 140. Alternatively, as shown in FIG. 4c, the snap-on device is a protrusion 173 centered at the bottom of the compartment 145, on the inner surface of the closed end 155. The protrusion 173 mates with a first end 170 the sized bore 165 of the ferrule adapter 160. In such a case, each compartment 145 has a different size snap-on device, i.e., protrusion 173, adapted for snapping into the first end 170 of the sized bore 165 (having a particular diameter) of a particular bit sizing ferrule adapter.

A second end 175 of the sized bore 165 located opposite the first end 170 has a lip 180 which extends beyond the diameters of the sized bore 165, the diameter of compartment 145 and the diameter of adjustable length bore 130. Furthermore, the lip 180 is thick. The large diameter and thickness of the lip 180 facilitate grasping the lip and pulling it from the bore 130 or from the cylindrical containers 140. Therefore, when the first end 170 of the bit sizing ferrule adapter 160 is inserted into the adjustable bore 130 or the compartment 145, the lip 180 rests on outer surfaces 182 or 183 around the periphery of the adjustable bore 130 and the compartment 145 respectively.

Figure 6:
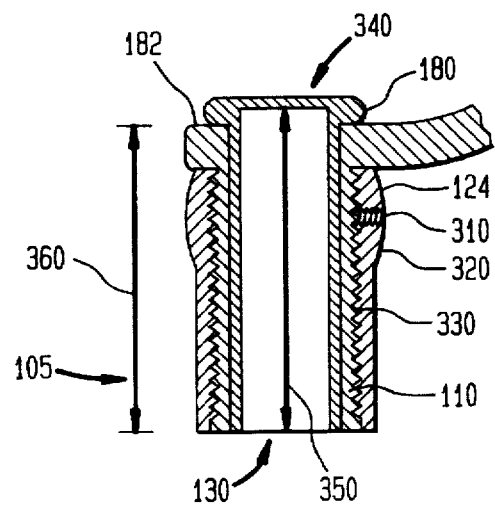
FIG. 6 illustrates a cross-sectional view of the sleeve of the drill guide of FIG. 5a in greater detail.

FIG. 6 shows in greater detail a bit sizing ferrule adapter 340 inserted into the adjustable bore 130 of the sleeve 105 which is in a fully retracted position. The lip 180 is seated on the outer surface 182 around the periphery of the adjustable bore 130. Thus, the lip 180 prevents the bit sizing ferrule adapter 340 from passing completely through the adjustable bore 130. Furthermore, the lip 180 provides a convenient area for gripping the bit sizing ferrule adapter 340 for removal from the adjustable bore 130 or the compartment 145 (FIG. 4a).

Illustratively, as shown in FIG. 6, the bit sizing ferrule adapter 340 has a length 350 which is approximately equal to the length 360 of the fully retracted sleeve 105. However the length 350 of the ferrule adapter 340 may be less than the length 360 of the fully retracted sleeve 105. Advantageously, a longer ferrule adapter 340 provides greater drill bit stability and more precise alignment.

The adjustment of the length of the sleeve 105 may be achieved as follows. The outer segment 115 is screwed onto the inner segment 110 and may retract or extend therefrom by turning the outer segment clockwise or counterclockwise direction 120 (i.e., screwing or unscrewing). The top end 122 of the outer segment 115 is shaped to form a depth adjusting nut 124. The depth adjusting nut 124 has a knurled grip 126 so that depth adjusting nut 124, which is an integral part of the outer segment 115, may be rotated more easily around the inner segment 110.

Figure 5A:
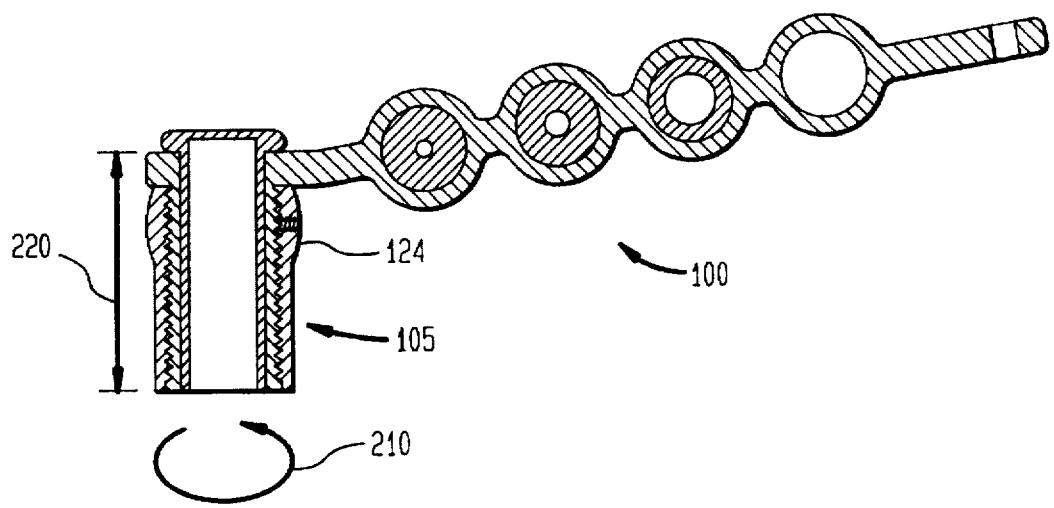
FIG. 5a illustrates a cross-sectional view of the drill guide of FIG. 4a in a retracted position.
Figure 5B:
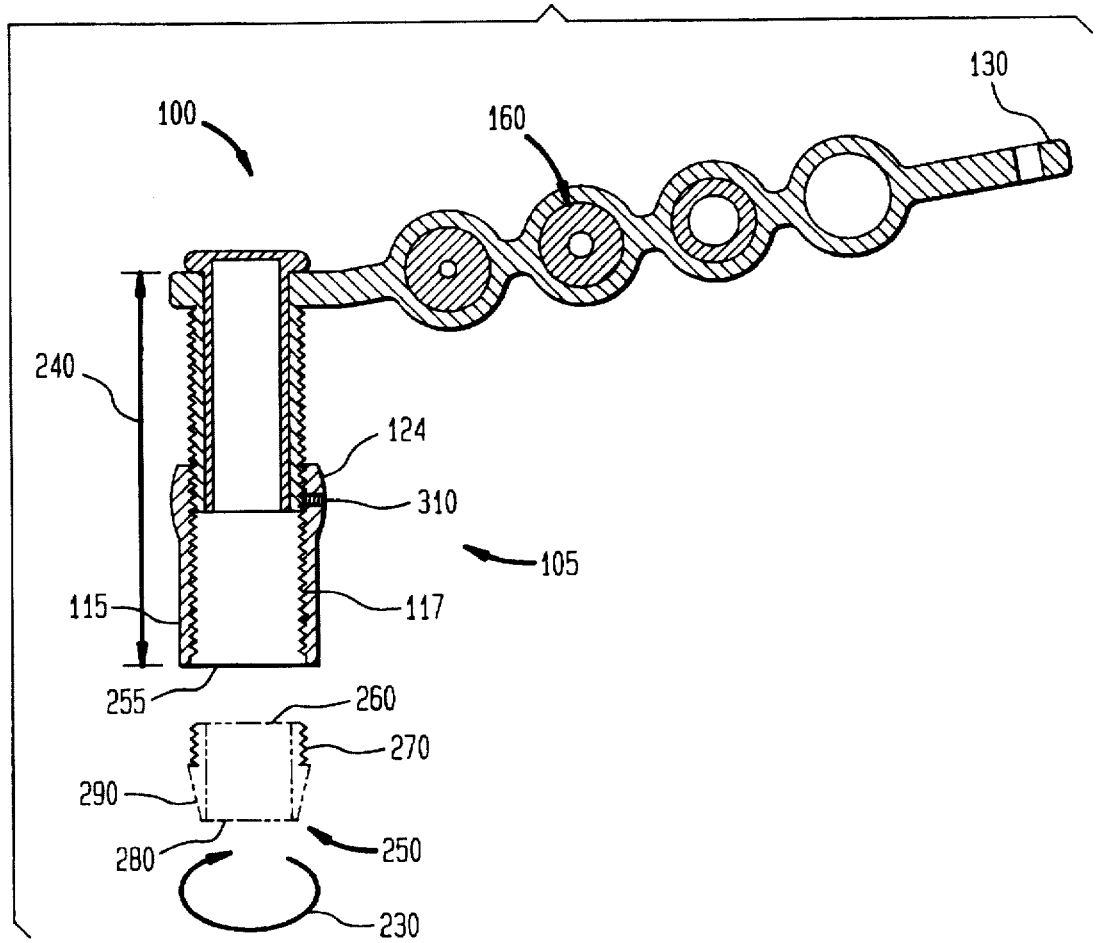
FIG. 5b illustrates a cross-sectional view of the drill guide of FIG. 4a in a fully extended position.

FIG. 5a and 5b show a cross-sectional view of the drill guide 100 shown in FIG. 4a. The cross-sectional view cuts through the body of the ferrules 160, therefore, the lips 180 of the ferrules 160 stored in the handle 135 are not shown. When the depth adjusting nut 124 is fully turned in one direction, e.g., counterclockwise 210, the sleeve 105 has a minimum length 220. FIG. 5a shows the drill guide 100 in a fully retracted position. Conversely, when the depth adjusting nut 124 is fully turned in the other direction, e.g., clockwise 230, the sleeve 105 has a maximum length 240. FIG. 5b shows the drill guide 100 in a fully extended position.

An extension sleeve 250 may be attached to a lower opening 255 of the outer telescopic segment 115 to further extend the sleeve 105 beyond its fully extended maximum length 240. The extension sleeve 250 may be used, for example, to drill holes of small depth into a material such as a bone. (The inventive drill guide 100 may be used for precision drilling of any material).

A first end 260 of the extension sleeve 250 has a threaded outer surface 270 which screws into the threaded inner walls 117 of the outer telescopic segment 115 at the lower opening 255. Illustratively, a second end 280 of the extension sleeve 250 has a tapered outer surface 290, being wider at the middle of the extension sleeve 250 and narrower at the lower opening 280. For example, at the lower opening 280, the outer surface 290 has a minimum width or thickness, forming the periphery of the lower opening 280.

FIG. 6 shows the sleeve 105 in greater detail in a fully retracted position. An insert 310 is located within the depth adjusting nut 124, between its outer wall 320 and the threaded inner wall 330 of the inner segment 110. Illustratively, the outer wall 320 of the depth adjusting nut 124 is curved. The insert 310 prevents slippage of the treads of the threaded inner wall 330. Other materials, such as stainless steel or brass, that will not readily catch on the drill bit or gall against the sleeve 105 may be used.

Figure 7A:
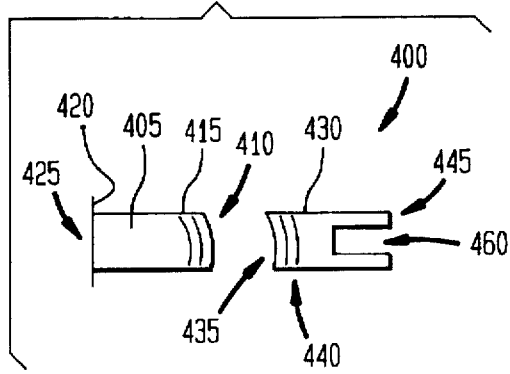
FIGS. 7a-7c illustrate a pair of the ferrule adapters which form a bit-length sizing ferrule adapter.
Figure 7B:
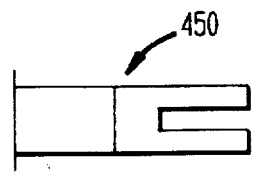
Figure 7C:
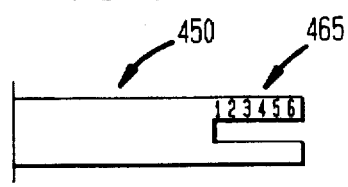

Illustratively, a pair of the ferrule adapters 400, shown in FIGS. 7a–c, are connected together for use in determining the length or depth of the hole drilled into the bone or any other material. The pair of the ferrule adapters 400 is used in adjusting the length of the sleeve 105 (FIGS. 4a–6) to thereby adjust the length of the exposed portion of the drill bit 170, 570 (FIGS. 4a, 8) which may protrude from the lower opening 255 of the outer telescopic segment 115 (FIG. 5b). (As discussed in greater detail below, during drilling of a bone or other material, only the exposed portion of the drill bit 170 extending beyond the lower opening 255 penetrates into the bone or other material, thus drilling a hole of a depth equalling the length of exposed portion.)

As shown in FIG. 7a, a first ferrule adapter 405 has an end 410 having a threaded outer surface 415 and a lip 420 on an opposite end 425. A second ferrule adapter 430 has an end 435 having a threaded inner surface 440 which mates with (e.g., screws into) the threaded outer surface 415 of the first ferrule adapter 405. This forms a bit-length sizing ferrule 450, shown in FIGS. 7b and 7c, used for determining the drill bit length which will be exposed from the sleeve 105 as shown in FIG. 8b.

An opposite end 445 of the second ferrule adapter 430 has a longitudinal slot 460 extending from the end 445 toward the threaded end 435. The surface of the second ferrule adapter 430 along the slot 460 is illustratively scored with markings 465 shown in FIG. 7c. These markings form a measuring scale or gauge useful in adjusting the length of the sleeve 105 (FIG. 4a). This in turn may be used to determine the exposed portion of the drill bit 170 (FIG. 4a) that may penetrate into the bone or other material. Once the length of the sleeve 105 is adjusted, the bit-length sizing ferrule 450 is no longer needed. Therefore, after measuring and adjusting the length of the sleeve 105, the bit-length sizing ferrule 450 is removed from the sleeve 105 and a ferrule having a proper width/diameter is inserted therein.

The bit-length sizing ferrule 450 is particularly useful for drill bits having a single uniform length. Many sets of drill bits used in medical application have the same standard length despite having different widths. For such cases, the markings on the bit-length sizing ferrule 450 indicate a specific exposed drill bit length. For example, a marking of 10 may indicate that 10 mm of the drill bit is exposed. Similarly, 20 mm of the drill bit is exposed for a marking of 20 and so on. For bits having differing lengths resulting in different bit lengths protruding from the chuck of the drill, placing the bit length protruding from the sleeve 105 up against a ruler provides a simple method for adjusting the length of the sleeve 105 to a desired length. Alternatively, the portion of the drill bit protruding from the sleeve 105 may be placed directly against the material to be drilled in order to set the length of the sleeve 105 as discussed below.

Figure 8A:
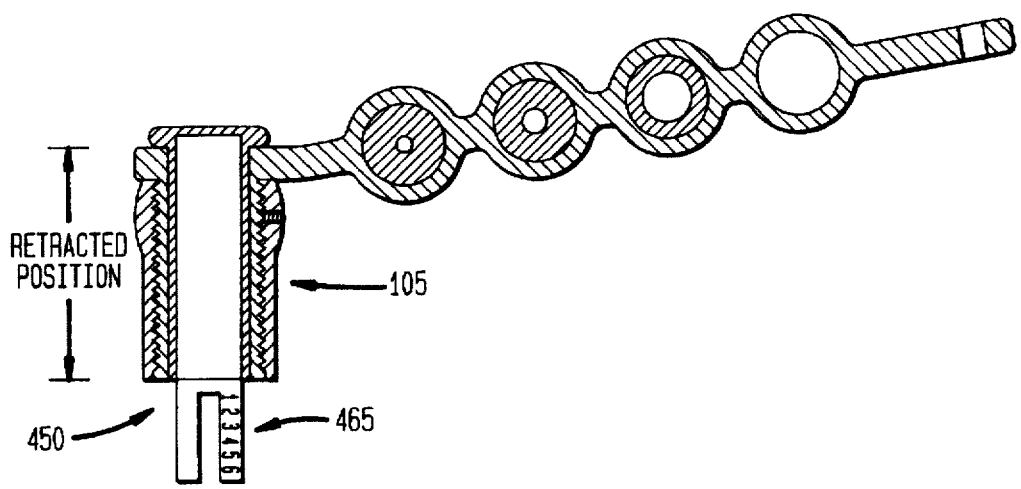
FIGS. 8a-8b illustrate a cross-sectional view of the drill guide of FIG. 4a with the bit-length sizing ferrule adapter of FIG. 7 inserted through the sleeve.
Figure 8B:
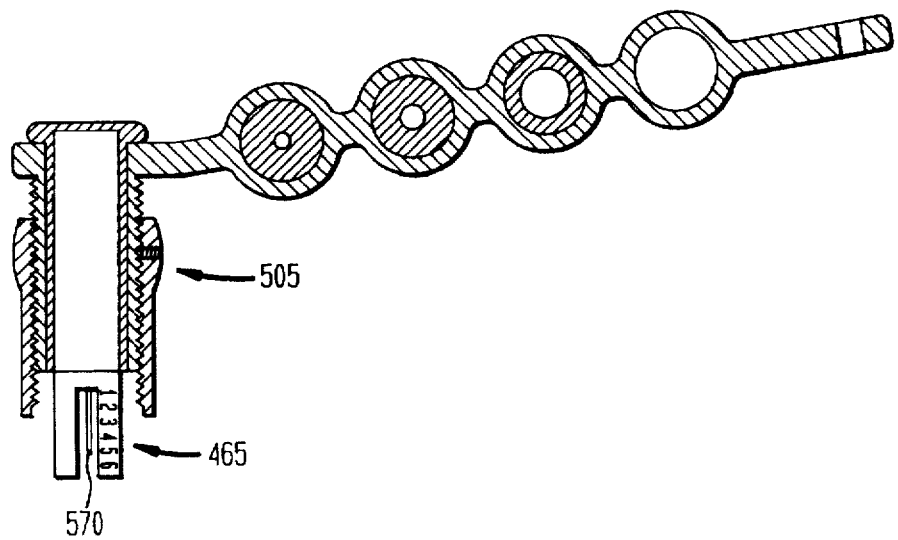

FIG. 8a shows the bit-length sizing ferrule 450 inserted into a fully retracted sleeve 105. The markings 465 extend beyond the fully retracted sleeve 105. When fully extended, the sleeve 105 will cover all of the markings 465. FIG. 8b shows a drill bit 570 inserted into a partially extended sleeve 505. With the aid of the markings 465, the sleeve 505 may be adjusted to expose a desired length of the drill bit 570.

Figure 9:
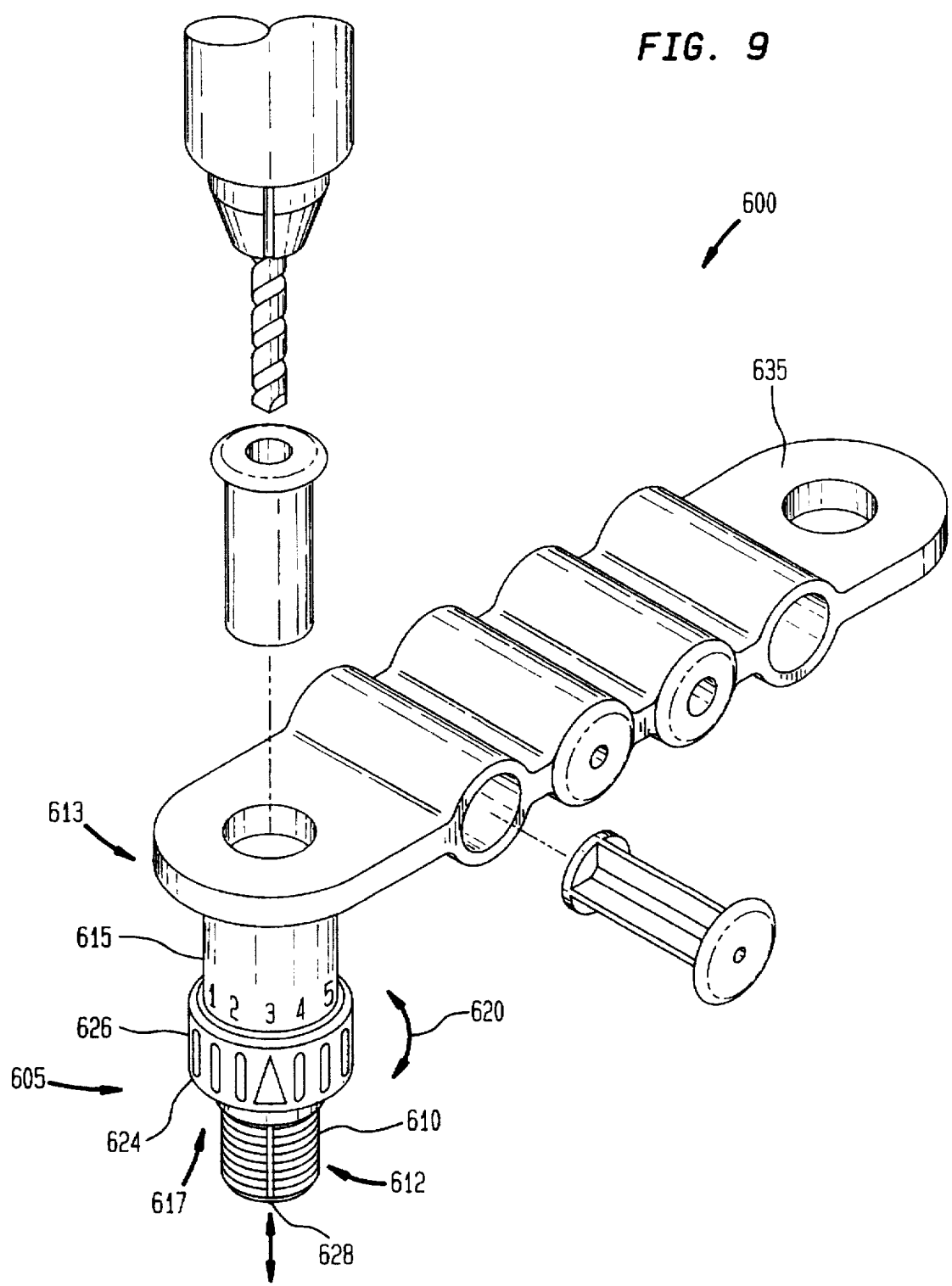
FIG. 9 illustrates a side elevation view of another embodiment of the drill guide with removable ferrules according to the invention.

FIGS. 9–11 shows another embodiment of the drill guide with removable ferrules 600 which embodiment is similar to the embodiment depicted in FIGS. 4a–7. The drill guide 600 differs from the drill guide 100 shown in FIGS. 4a–7 in that the handle 635 is connected to one end 613 of the outer segment 615. A depth adjusting nut 624 is attached to the other end 617 of the outer segment 615 on the outer surface. The inner surface 717 (FIG. 10b) of the outer segment 615 is smooth without any threads. Illustratively, the inner surface 717 has a key 725 (FIG. 10b).

The inner segment 610 has a threaded outer surface 612 and is screwed into the depth adjusting nut 624. The inner segment 610 retracts or extends from the outer segment 615 by turning the depth adjusting nut 624 in a clockwise or counterclockwise direction 620 (i.e., screwing or unscrewing). When the depth adjusting nut 624 is turned for example in the clockwise direction, the inner segment 610 retracts into the outer segment 615. Illustratively, markings may be provided on the outer surface of the outer segment 615 for depth gauging. The depth adjusting nut 624 has a knurled grip 626 to facilitate the rotation of the depth adjusting nut 624 thereby adjusting the length of the sleeve 605.

The threaded outer surface 612 of the inner segment 610 has a keyway 628 (FIG. 9) located along the length of the inner segment 610. The functions of the keyway 628 and the key 725 (FIG. 10b) are explained with reference to FIG. 10c. The key 725 and keyway 628 translate the rotation of the nut 624 into an extension of the inner segment 610. That is, as the nut 624 is rotated, the inner segment 610 experiences a torque in the direction of rotation. As shown in FIG. 10c, a key 725 inserted in the keyway 628 bears against edges 735 of the keyway 628 (FIG. 9) along the threaded outer surface 612 of the inner segment 610. This prevents the inner segment 610 from rotating with the nut 624. Instead, the edges 735 transmit a normalizing force to the key 725, which in turn causes the threads of the inner segment 610 to slide with respect to the threads of the nut 624, thereby retracting or extending the inner segment 610 with the rotation of the nut 624.

FIG. 10a and 10b show a cross-sectional view of the drill guide 600 shown in FIG. 9. When the depth adjusting nut 624 is fully turned in one direction, e.g., clockwise, the sleeve 605 has a minimum length 720. FIG. 10a and FIG. 11 show the drill guide 600 in a fully retracted position. Conversely, when the depth adjusting nut 624 is fully turned in the other direction, e.g., counterclockwise, the sleeve 605 has a maximum length 740. FIG. 10b shows the drill guide 600 in a fully extended position.

An extension sleeve 750 may be attached to a lower opening 755 of the inner telescopic segment 610 to further extend the sleeve 605 beyond its fully extended maximum length 740. A first end 760 of the extension sleeve 750 has a threaded inner surface 770 which screws onto the threaded outer walls 612 of the inner telescopic segment 610 at the lower opening 755. Illustratively, a second end 780 of the extension sleeve 750 has a tapered outer surface 790, being wider at the middle of the extension sleeve 750 and narrower at the lower opening 780. For example, at the lower opening 780, the outer surface 790 has a minimum width or thickness, forming the periphery of the lower opening 780.

Figure 12A:
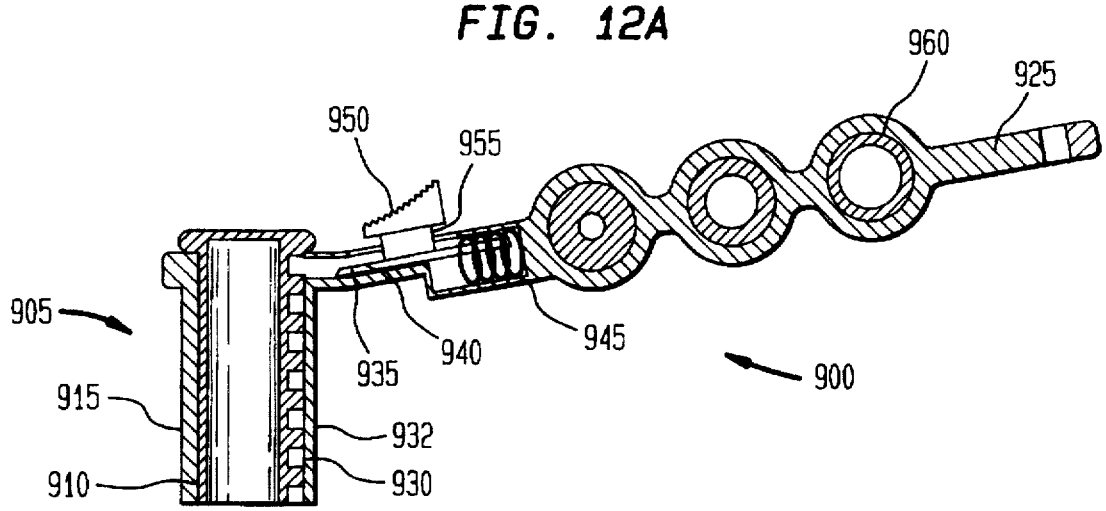
FIG. 12a illustrates a cross-sectional view of a third embodiment of the drill guide with removable ferrules according to the invention.

FIG. 12a illustrates yet another embodiment of the drill guide 900 according to the invention. The drill guide 900 has an adjustable length sleeve 905 formed by an inner segment 910 and an outer segment 915. The outer segment 915 is attached to the handle 925. The outer surface of the inner segment 910 has equal spaced teeth 930 extending in the vertical direction. The teeth (or ribs) 930 are separated by depressions 932 which receive a tip 935 of a spring loaded rod 940. (Alternatively, instead of teeth/ribs 930 and depressions 932, dimples 932 could be formed in the outer surface of the inner segment 910.) A spring 945 at the opposite end of the tip 935 biases the tip 935 to engage the teeth by contacting a depression (or dimples) 932 between two adjacent teeth 930. This holds the inner telescopic segment 910 at a desired insertion within the outer segment 915. A lever 950 is attached to the spring loaded rod 940 via leg 955.

The length of the sleeve 905 is adjusted as follows. Using a finger of the hand which grips the handle 925, the operator urges, i.e., pushes back, the lever 950 against the bias of the spring 945. This disengages the tip 935 from the teeth 930 and allows the inner telescopic segment 910 to freely slide within the outer segment 915. To extend the sleeve 905, the operator grips the inner telescopic segment 910 using his or her other hand, and retracts the inner telescopic segment 910 so that the sleeve 905 has the desired overall length. In this embodiment, the ferrules 960 have a taller lip to facilitate grasping thereof.

Thereafter, the lever 950 is released so that the tension in the spring 945 biases the tip 935 against the outer surface of the inner telescopic segment 910. The tip 935 engages the teeth thereby preventing the inner telescopic segment 910 from sliding within the outer segment 915. The tension of the spring 945 keeps the tip 935 securely engaged with the teeth 930. Once the length of the sleeve 905 is properly adjusted, a ferrule 960 having a smooth outer surface is inserted into the drill guide 900. Thereafter, the drill guide 900 is positioned with the exposed end of the inner telescopic segment 910 touching the bone or other material.

Figure 12B:
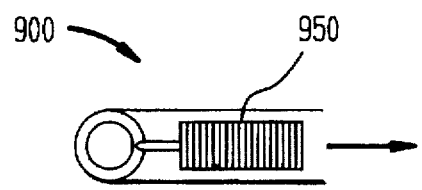

FIG. 12b shows a top view of the guide 900. The lever 950 has a rough serrated upper surface where the finger contacts the lever 950 for pushing back the lever 950.

Figure 13A:
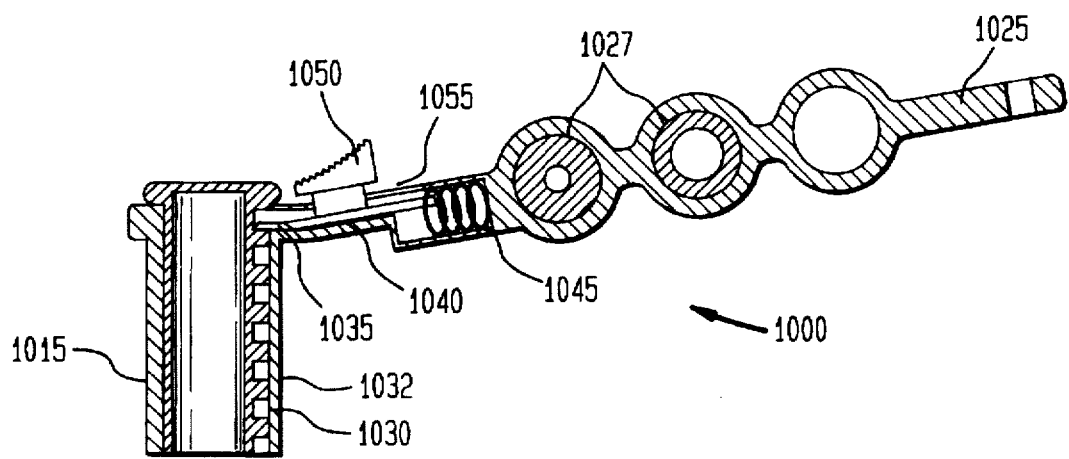
FIG. 13a illustrates a cross-sectional view of yet another embodiment of the drill guide with removable ferrules according to the invention.

FIG. 13a illustrates another embodiment of the drill guide 1000 which is similar to the embodiment depicted in FIG. 12a. Instead of having an inner an outer segments, as the drill guide 900 of FIG. 12a, the drill guide 1000 has a single segment sleeve 1015 attached to the handle 1025. The sleeve 1015 serves an analogous function as the outer segment 915 of the drill guide 900 shown in FIG. 12a. Instead of the inner segment 910 of FIG. 12a, the ferrules 1027 themselves have an outer surface with equal spaced teeth 1030 separated by depressions 1032. The remaining elements are identical to those described in FIGS. 12a and 12b. That is, a tip 1035 of a spring loaded rod 1040 engages the teeth 1030 and holds the ferrule 1027 at a desired insertion. A lever 1050 is provided which is attached to the rod 1040 by a leg 1055. The lever may be urged against the bias of the spring 1045 for disengaging the tip 1035 from the teeth 1030.

The lever 1050 is pushed back against the bias of the spring 1045 to allow insertion of a bit sizing ferrule 1027 into the segment 1015. Once the bit sizing ferrule 1027 is inserted to achieve a desired overall length of the sleeve 1015, the lever 1050 is released to engage the tip 1035 with the teeth 1030.

The telescopic inner segment 910 (FIG. 12a) and the bit sizing ferrules 1027 (FIG. 13a) may have markings for measuring the length of the combination of the outer segment 915, 1015 with the telescopic sleeve 905 (FIG. 12a) or with the inserted ferrule 1027 (FIG. 13a). This is advantageous because the operator can adjust the length (which adjusts the penetration depth of the drill bit into the bone or material) and interchange different sized ferrules (which keeps the drill bit aligned and centered) without having to remove drill guide from the incision. Unlike the drill guides 100 (FIG. 4a) and 600 (FIG. 9), the segments abutting the incision do not rotate or move, thus minimizing trauma to the incision.

Figure 13B:
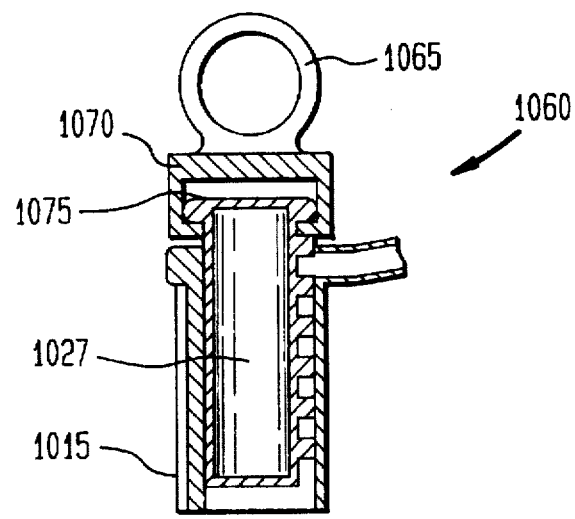
FIGS. 13b–13d illustrate a cross-sectional view of a ferrule extractor.

FIG. 13b shows a ferrule extractor 1060 having a handle or a grip 1065 and a head or a crown 1070. The head 1070 is shaped to slide onto the lip 1075 of the ferrule 1027. After sliding the head 1070 onto the lip 1075, the ferrule extractor 1060 is pulled from its handle 1065 to extract the ferrule 1027 from the segment 1015. The ferrule extractor 1060 may also be used for extracting ferrules stored in the handle 1025 of the drill guide 1000.

Figure 13C:
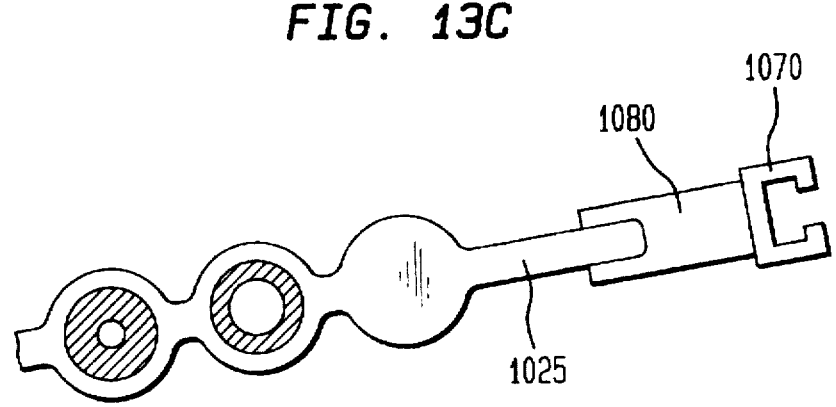
Figure 13D:
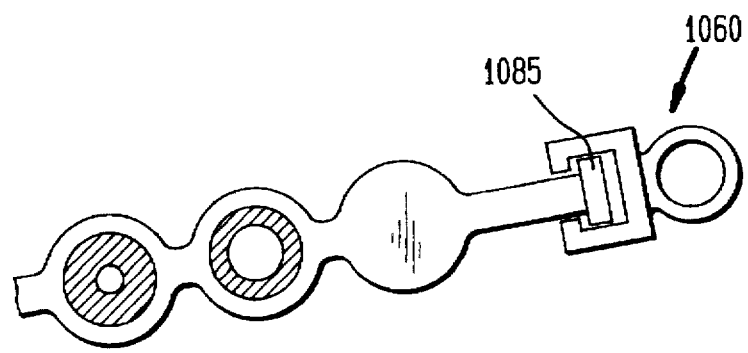

The handle 1065 of the ferrule extractor 1060 may be a round loop to allow insertion of a finger used in pulling ferrule extractor 1060 during extraction of a ferrule. Alternatively, as shown in FIG. 13c, the handle 1065 may have a hollow straight body 1080 used for storing the ferrule extractor 1060 at the end of the handle 1025 of the drill guide 1000. The straight body 1080 is dimensioned to slide onto the handle 1025 of the drill guide 1000. FIG. 13d shows the handle 1065 having a lip 1085 similar to the lip 1075 of the ferrule 1027. The ferrule extractor 1060 may be stored on the handle 1065 by snapping the head 1070 of the extractor 1060 onto to lip 1075 of the handle 1065.

Figure 14A:
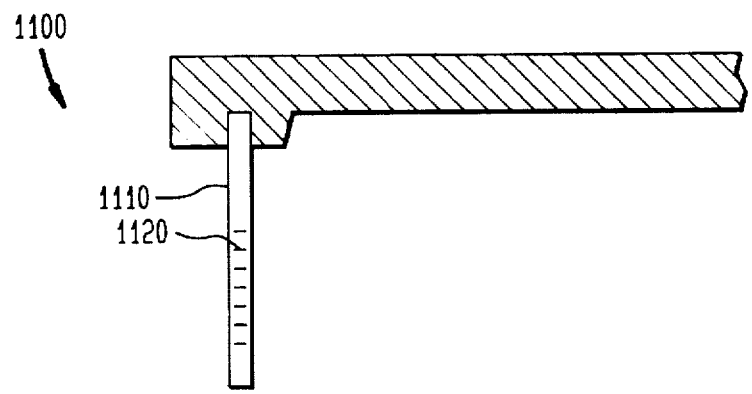
FIG. 14a illustrates a cross-sectional view of a prior art right angle drill.
Figure 14B:
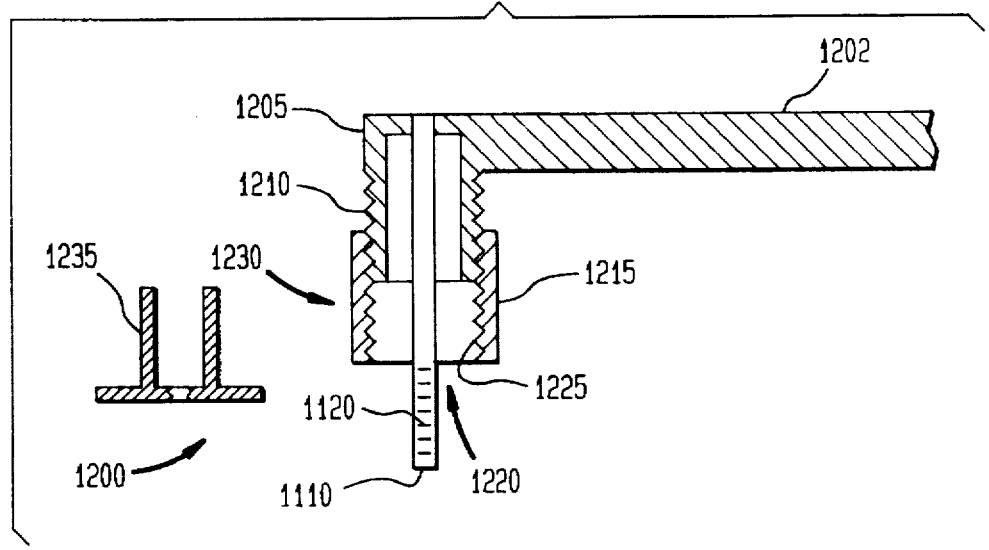
FIGS. 14b–14c illustrate a cross-sectional view of an embodiment of a right angle drill according to the present invention.

The aspects of the present invention described above may also be combined with a drill. FIG. 14a shows a conventional right angle drill 1100 with a drill bit 1110 attached thereto. The drill bit 1110 has marking 1120 as is often the case for drill bits used in medical applications. Such drill bits are available from, for example, NobelPharma of Chicago, Ill. and Implant Innovations of Palm Beach, Fla. FIG. 14b shows a right angle drill 1200 according to the present invention. The drill 1200 has a neck 1202. The neck 1202 terminates with a head 1205. The head 1205 has threaded outer walls 1210. An outer segment 1215 has a bore 1220 passing therethrough and has threaded inner walls 1225. The outer segment 1215 is screwed onto the threaded outer walls 1210 of the drill head 1205 to form an adjustable length sleeve 1230. As shown, the adjustable length sleeve 1230 has a bore 1220 which is axially aligned with the drill bit 1110 (inserted therethrough). Illustratively, the bore 1220 of the adjustable length sleeve 1230 is dimensioned to receive therethrough a bit sizing ferrule adapter 1235.

Figure 14C:
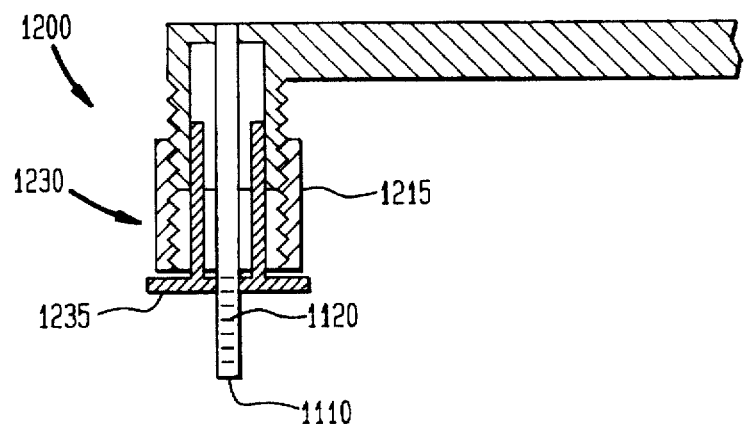

The marking 1120 on the drill bit 1110 are used to adjust the length of the sleeve 1230. Alternatively, when using drill bits without markings, the length of the sleeve 1230 is adjusted in a similar fashion as the sleeve 105 of FIGS. 4a–7. That is, the outer segment 1215 is turned to adjust the length of the sleeve 1230. As depicted in FIG. 14c, the ferrule adapter 1235 is inserted into the sleeve 1230. Illustratively, the inserted ferrule adapter 1235 has markings and is used for depth sizing.

With a properly sized ferrule adapter and a properly adjusted sleeve length, a bone or other material may be drilled to produce a properly centered and aligned hole having a desired depth and angle. By adjusting the length of the sleeve 1230 to a desired length, using the depth sizing ferrule adapter 1235, a precise dimensioned and angled hole may be drilled. Successively inserting the depth sizing ferrule adapter 1235 into the bore 1220 and adjusting the length of the sleeve 1230, a pre-drilled hole may be enlarged or additional holes of different widths and depths may be drilled.

Figure 15A:
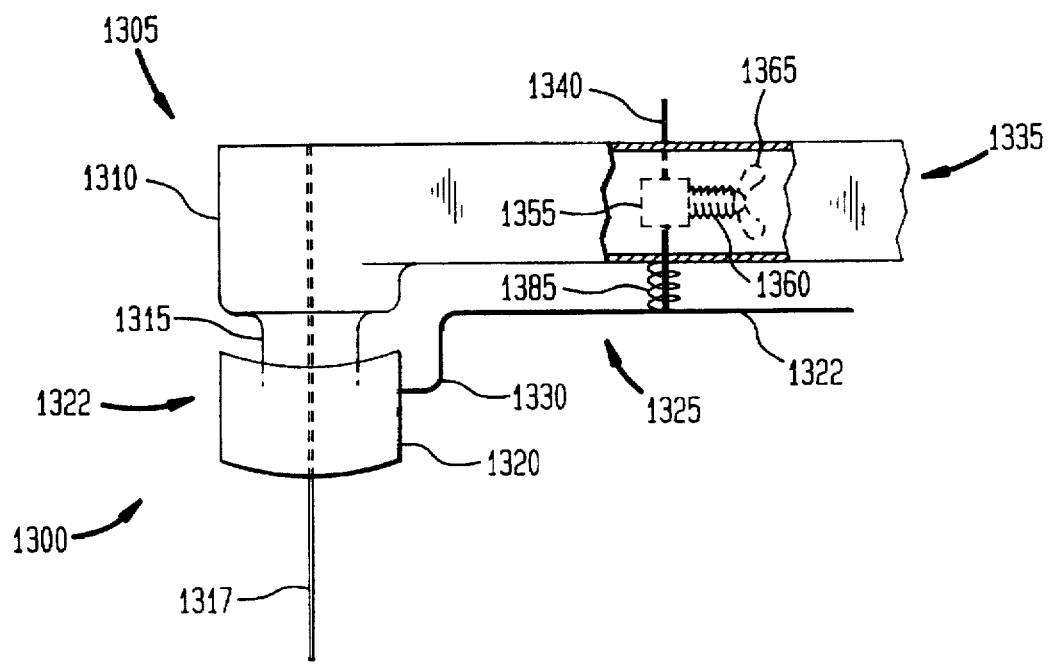
FIG. 15a illustrates a cross-sectional view of another embodiment of the right angle drill according to the present invention.

FIGS. 15 and 16 show different embodiments of a right angle drill. In the embodiment shown in FIG. 15a, a right angle drill 1300 has an end 1305 having a wide top end 1310 and a narrow bottom end 1315. A drill bit 1317 is attached to the top end 1310. An outer segment 1320 having the same width as the top end 1310 is inserted over the narrow bottom end 1315 to define an adjustable length sleeve 1322.

The narrow bottom end 1315 is held in place by a retaining mechanism 1325. Illustratively, the retaining mechanism 1325 is shaped to follow the contour of the right angle drill 1300 and has one end 1330 attached to the outer segment 1320. The retaining mechanism 1325 has a portion 1332 parallel to the handle 1335 of the drill 1300. An appendage 1340 is attached to the parallel portion 1332 of the retaining mechanism 1325.

Figure 15B:
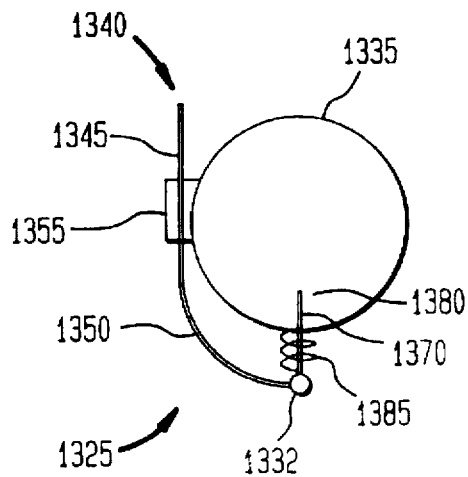
Figure 15C:
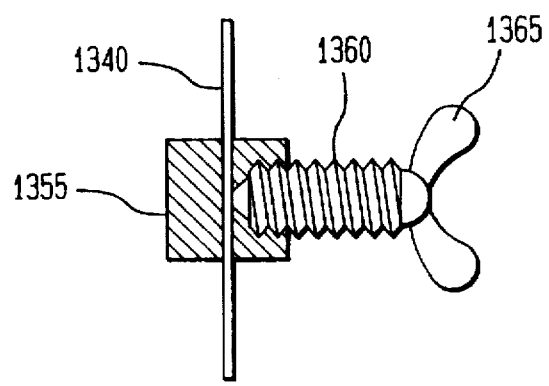

As shown in FIG. 15b, the appendage 1340 has a vertical portion 1345 and a curved portion 1350 which is contoured around the handle 1335. The vertical portion 1345 of the appendage 1340 passes through a retaining body 1355 as shown in greater detail in FIG. 15c. The retaining body 1355 has a screw 1360 which, when tightened, holds the appendage 1340 in place. Loosening the screw 1360 allows the appendage 1340 to freely move through the retaining body 1355. Illustratively, the screw 1360 has a butterfly end 1365 for easy grasping and turning.

The retaining mechanism 1325 also has a rod 1370 which has one end 1375 attached to the parallel portion 1332 of the retaining mechanism 1325. In the embodiment shown in FIG. 15b, the other end of the rod 1370 passed through a hole into the handle 1335. The rod 1370 may be spring loaded by a spring 1385. The spring 1385 is coiled around the rod 1370 between the parallel portion 1332 of the retaining mechanism 1325 and the handle 1335.

The length of the sleeve 1322 (FIG. 15a) is adjusted as follows. The screw 1350 is loosened and the appendage 1340 moved up or down through the retaining body 1345 until the desired length of the sleeve 1322 is achieved. Thereafter, the screw 1350 is tightened to prevent the appendage 1340 and the attached outer segment 1320 from moving. This fixes the length of the sleeve 1322.

In the case of a spring loaded appendage 1340, when the screw 1350 is loosened, the tension in the spring (1385, 1445, 1450, 1535 or 1550) forces the outer segment 1320 away from the narrow bottom end 1315 of the drill end 1305, thus increasing the length of the sleeve 1322. To decrease the length of the sleeve 1322, after the screw 1350 is loosened, the appendage 1340 or the attached outer segment 1320 is pushed against the tension of the spring. When the desired length of the sleeve 1322 is achieved, the screw 1350 tightened to fix the length of the sleeve 1322.

Figure 16A:
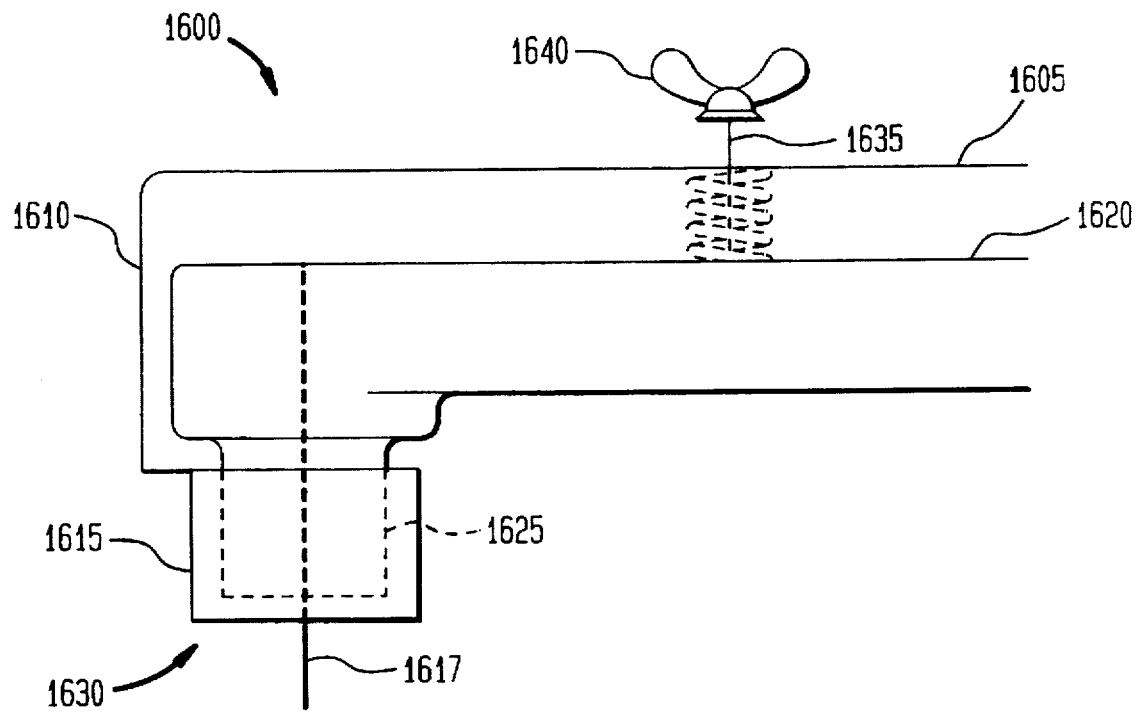
FIG. 16a illustrates a cross-sectional view of yet another embodiment of the right angle drill according to the present invention.

FIG. 16a shows a right angle drill 1600 similar to the embodiment shown in FIG. 15. The right angle drill 1600 has an outer body 1605 having a wide top end 1610 and a narrow bottom end 1615. A drill bit 1617 is attached to an inner body 1620. The inner body 1620 is located inside the outer body 1605. The inner body 1620 is contoured to have a similar shape as the outer body 1605. However, the inner body 1620 has a shorter narrow bottom end 1625 than the narrow bottom end 1615 of the outer body 1605. The short inner bottom end 1625 and the long outer bottom end 1615 define an adjustable length sleeve 1630.

Figure 16B:
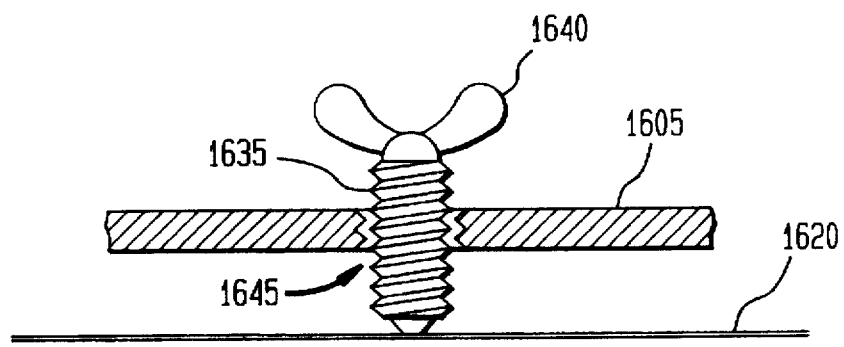

The outer body 1605 is attached to the inner body 1620 by a retaining mechanism. Illustratively, the retaining mechanism is a screw 1635 having a butterfly end 1640 as shown in FIG. 16b. The screw 1635 is pivotally attached to the inner body 1620 and passes through a threaded hole 1645 in the outer body 1605. The length of the sleeve 1630 is adjusted by turning the screw 1635. As the screw 1635 turns within the threaded hole 1645, the outer body 1605 moves up or down thus changing the length of the sleeve 1630. As described in connection with FIG. 14c, a ferrule adapter may be inserted into the sleeves 1322, 1630 (FIGS. 15a, 16a). In the drills 1300, 1600 shown above, a slotted drill guide is presumed which has a non-adjustable slot for receiving and retaining drill bits.

Figure 17A:
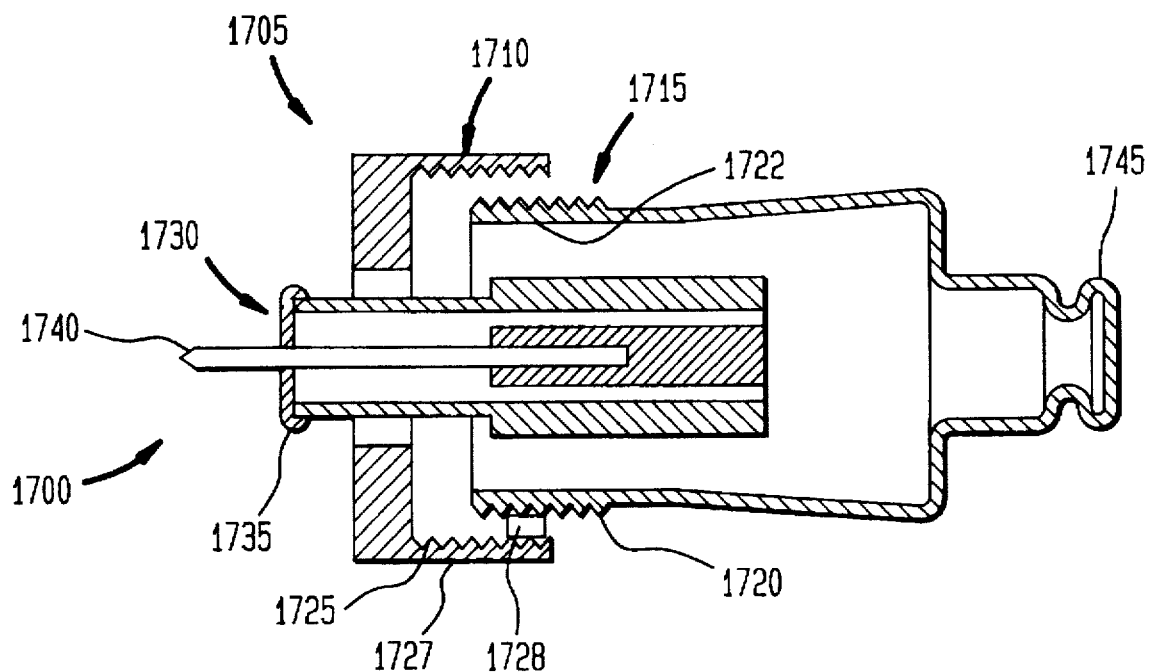
FIGS. 17a–17b illustrate a cross-sectional view of a universal chuck having an adjustable sleeve according to the present invention.

FIG. 17a shows yet another embodiment of the present invention for use with a universal chuck 1700. In medical applications, the universal chuck 1700 is often referred to as a Jacobs chuck. The universal chuck 1700 has an adapter 1745 which fits into the retaining slot of the drill 1100. The universal chuck 1700 has an adjustable sleeve 1705. The adjustable sleeve 1705 is similar to the adjustable sleeve 105 shown in FIGS. 4a–6. That is, the adjustable sleeve 1705 has an outer segment 1710 which is screwed onto a inner segment 1715. The inner segment 1715 is attached to the universal chuck 1700 and has a threaded outer walls 1720 and smooth inner walls 1722. The outer segment 1710 has a threaded inner walls 1725 and smooth outer walls 1727. The threaded inner walls 1725 mate with the threaded outer walls 1720 of the inner segment 1715. An insert 1728, similar to the insert 310 of FIG. 6, is located between the threaded walls 1720 and 1725. The insert 1728 prevents slippage of the treads.

Figure 17B:
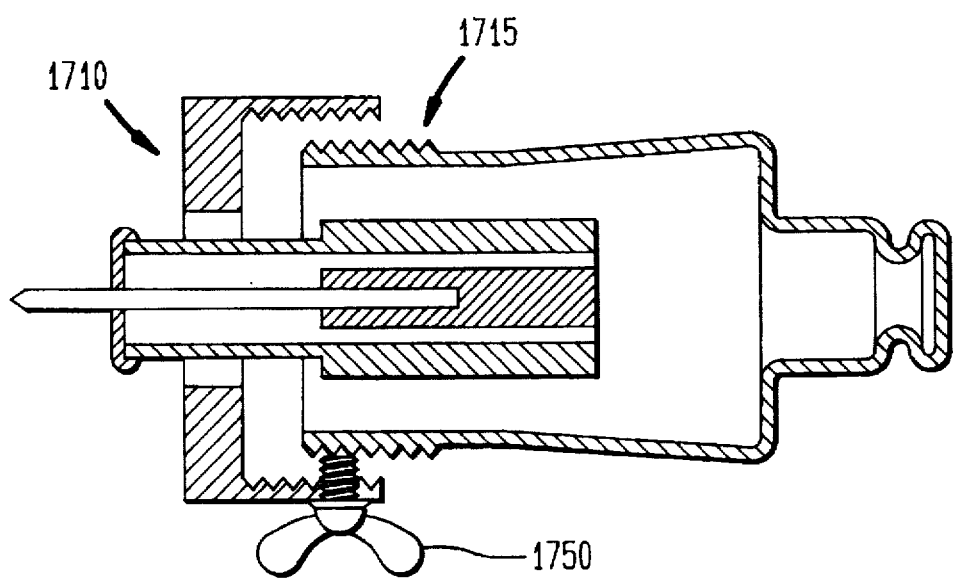

Alternatively, the inner and outer segments 1715, 1710 do not have walls with an inner or outer smooth surfaces 1722, 1727. Rather, the threads extend through both the inner and outer surfaces of the walls of each the inner and outer segments 1715, 1710 as shown in FIG. 17b. Instead of the insert 1728, a wing nut 1750 may be used to prevent slippage of the treads. Tightening the wing nut 1750 presses together the outer and inner segments 1710, 1715 and fixes the length of the adjustable sleeve 1705.

The length of the adjustable sleeve 1705 is adjusted by turning the outer segment 1710. This is similar to the length adjustment of the adjustable sleeve 105 of FIGS. 4a–6. As with the adjustable sleeve 105 of FIGS. 4a–6, the adjustable sleeve 1705 has a bore 1730 designed to receive a bit sizing ferrule adapter 1735. A drill bit 1740 in inserted into the universal chuck 1700 through the bore 1730.

Figure 18A:
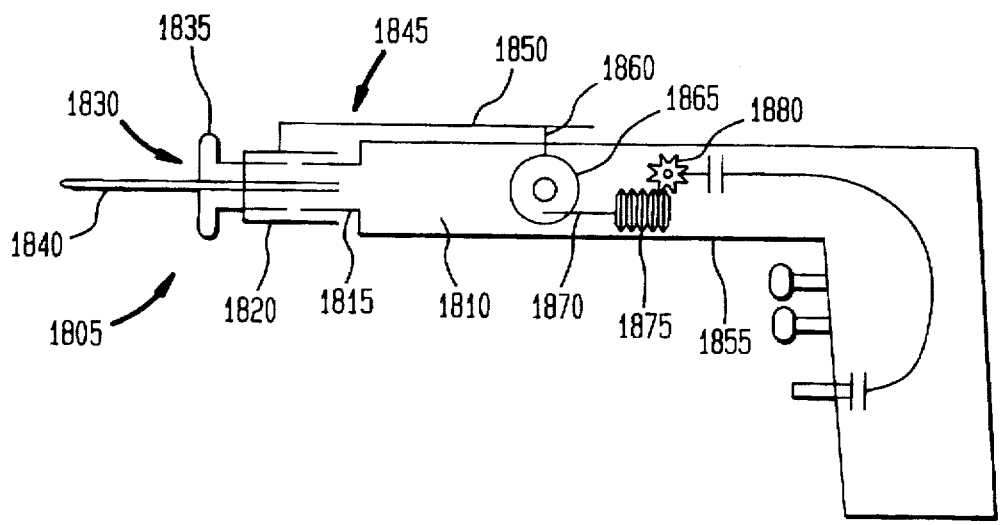
FIGS. 18a–18c illustrate a cross-sectional view of pistol grip drill having an adjustable sleeve according to the present invention.
Figure 18B:
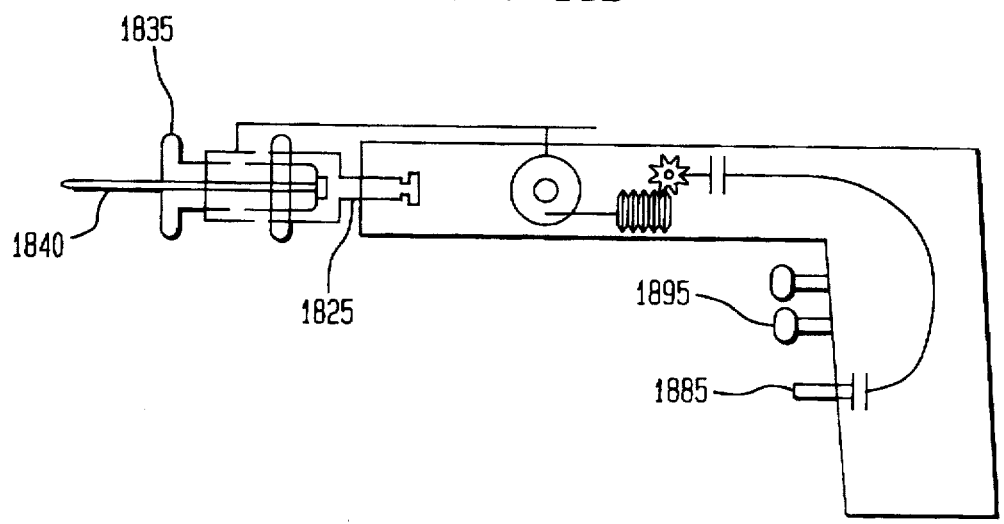

FIG. 18a shows a pistol grip drill 1800 embodiment of the present invention. The pistol grip drill 1800 has an adjustable length sleeve 1805 attached to the drill head 1810. The adjustable sleeve 1805 is similar to the adjustable length sleeve 1322 shown in FIG. 15a. That is, the adjustable sleeve 1805 has an inner segment 1815 and an outer segment 1820. Both inner and outer segments 1815, 1820 have smooth walls. The inner segment 1815 is attached to the drill head 1810. Alternatively, inner segment 1815 is attached to a removable universal chuck 1825 as shown in FIG. 18b. The adjustable sleeve 1805 has bore 1830 for receiving a bit sizing ferrule adapter 1835 (FIG. 18b) and a drill bit 1840.

The outer segment 1820 is slidably inserted over the inner segment 1815 and is attached to a retaining mechanism 1845. In this embodiment, the retaining mechanism 1845 is a motorized retaining mechanism. This motorized embodiment can be use in a computer assisted surgical drilling or computer operated drill presses for drilling into other material such as wood, metal or plastic.

Illustratively, the retaining mechanism 1845 has a rod 1850 parallel to the neck 1855 of the drill 1800. An attaching rod 1860 connects the parallel rod 1850 to a disc 1865. The disc 1865 is rotatably mounted on the neck 1855 of the drill 1800. Rotating the disc 1865 cause backward or forward movement in the parallel rod 1850. This changes the length of the adjustable sleeve 1805.

To rotate the disc 1865, a toothed rod 1870 has one end attached to the disc 1865. The other end of the toothed rod 1870 has teeth 1875 that mesh with a gear 1880. The gear 1880 is motorized and turns when an adjustment switch 1885 is depressed. For easy access, the switch 1885 is located on the handle 1890 of the drill 1800. This allows changing the length of the adjustable sleeve 1805 using a single hand; the hand that is grasping the handle 1890. Once the desired length of the adjustable sleeve 1805 is obtained, the operator stops depressing the adjustment switch 1885 and presses the on switch 1890 to activate the drill 1800 and begin drilling.

Figure 18C:
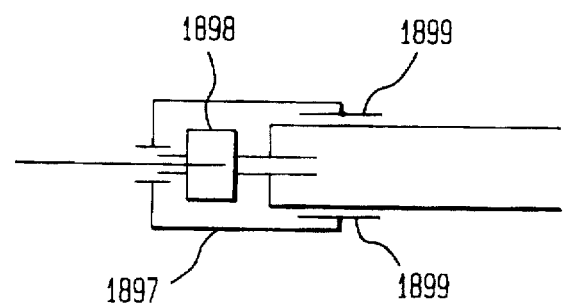

FIG. 18c shows a top view of an alternate retaining mechanism for the adjustable sleeve 1805. (In this case, a slotted drill bit retention mechanism 1898 is shown). In this embodiment, two parallel rods 1897 are used instead of the single parallel rod 1850 of FIGS. 18a and 18b. As shown, the rods 1897 are guided by guides 1899. Using two parallel rods provides a more stable adjustable sleeve 1805.

Illustrative Applications

The operation of the inventive drill guide is as follows. For simplicity, the remaining explanation will be confined to the drill guide 100 but is equally applicable to the other embodiments detailed herein.

Medical Applications

The operation of the inventive drill guide 100 will now be explained in a medical field context.

An incision is made in the region of the fracture and the bones are reduced to their correct anatomical positions. The operator then selects a bit sizing ferrule adapter 160 having an inner bore 165 matching the width of a drill bit to be used to drill a desired width hole. While holding the handle 135 with one end, the operator grasps the selected ferrule 160 with the other hand and inserts the selected ferrule 160 into the handle end of the bore 130 of the sleeve 105 until the lip 180 rests on the outer surface 182 of the sleeve 105. The operator then inserts the sleeve end opposite the surface 182 into the incision until that inserted end contacts the bone. The operator aligns the drill guide properly and inserts a drill bit 170 into the end of the bore 165 proximate to the lip 180. The operator then drills the hole to a desired depth.

As mentioned above, the drill guide 100 is adapted for adjusting the length of the sleeve 105 to restrict the amount of the drill bit which is exposed from the end of the bore 130 opposite the surface 182. This in turn restricts the penetration depth of the drill bit 170 to the length of the drill bit which is exposed when the coupling of the drill abuts the lip 180 of the bit sizing ferrule adapter 160. The above procedure may therefore be modified as follows. After inserting the correct width bit-sizing ferrule 160, but before drilling into the bone, the operator adjusts the overall length of the sleeve 105. This can be achieved in a number of ways. For example, assume that the desired drilling depth is known (for instance, by sliding a depth gauge over a guide wire previously inserted into the bone). The operator inserts the drill bit into the bore 130 until the coupling meets the lip 180 and then slides a depth gauge on the exposed portion of the drill bit. Alternatively, the operator may use the two-piece ferrule 400 as discussed above. In yet another embodiment, the outer surface of the inner segment contains markings which indicate the exposed length of the drill bit. The operator then adjusts the overall length of the sleeve so that a predetermined length of drill bit protrudes from the end of the sleeve 105 opposite the surface 182 when the coupling of the drill abuts the lip 180 of the bit-sizing ferrule adapter 160. Once adjusted, the operator commences drilling the hole as outlined above until the coupling of the drill abuts the lip 180 of the bit sizing ferrule adapter 160. The drill guide 100, by virtue of being positioned between the material, e.g. the bone to be drilled, and the coupling, acts as a stop. This is because the sized bore 165 of the ferrule 160 is large enough to accept the drill bit but not large enough to accept the quick coupling. Furthermore, the distal end of the drill guide opposite the surface 182 is blunt and too big to fit into the hole formed by the drill bit.

In a typical operation, several different width drill bits must be used. A particular advantage of the drill guide 100 is that the operator need not put down the drill guide 100 to adapt it for wider bits. For instance, in the aforementioned bone fixation procedure, it is desired to drill a narrow depth hole for inserting a guide wire and then to drill a larger width hole centered on the guide wire using a wider diameter cannulated drill bit. Such a procedure proceeds as follows. The operator inserts a narrow bore 165 bit sizing ferrule adapter 160 into the sleeve 105 (as mentioned above) and drills a hole in the bone for receiving a guide wire. The guide wire is then inserted into the hole. While grasping the handle 135 with one hand, the operator then removes the bit sizing ferrule adapter 160 with the other hand and replaces it with a bit sizing ferrule adapter with a wider bore 165 corresponding to the width of the cannulated drill bit. The operator then inserts the cannulated drill bit into the bore 165 of the selected ferrule 165 so that the guide wire is within the bore of the cannulated drill bit. Thereafter, the operator drills the correct depth hole using the cannulated drill bit as guided by the guide wire.

After the hole is drilled, the drill bit is withdrawn and the ferrule located in the sleeve 105 is replaced, as described above, with another ferrule having a width that is large enough to receive a surgical screw and tightening instrument. For example, a self-tapping surgical screw is inserted through the ferrule located in the sleeve 105 and screwed into the bone. As needed, the ferrule adapter 160 located in the sleeve 105 is interchanged with a properly sized ferrule adapter 160 (illustratively stored in the handle 135). Preferably, the screw is first secured to a screwdriver which is then inserted through the adjustable bore 130 and over the guide wire.

The depth of the hole is known because it is the same as the exposed drill bit as adjusted by the operator. This enables the operator to select a screw of the precise required length. In addition, the drill guide 100 may be used for tapping or countersinking the hole prior to inserting the screw. In such a case, a properly sized ferrule adapter 160 is inserted into the adjustable bore 130. Next, an appropriate instrument, e.g., tap, countersink, etc., may be inserted into the ferrule adapter located in the adjustable bore 130 and thereby guided by the drill guide 100. After the screw is inserted, the guide wire is withdrawn. Alternatively, the drill guide may be used without a guide wire, and the screw inserted through the adjustable bore 130 of the drill guide 100.

An illustrative example, where the drill guide 100 (FIG. 4a) is used in preparing an implant sites 1910 in root form implant surgery, is now described. (Branemark, Zarb, Albrektsson "Tissue Integrated Prosthesis", Quintessence, Chicago (1987) describes a general surgical procedure for attaching screw type implants. Misch, "Contemporary Implant Dentistry", Mosby, St. Louis (1993) discloses a general surgical procedure for attaching cylindrical press-fit implants. Bell (Ed.), "Modern Practice Orthognathic and Reconstructive Surgery", WB Saunders, Philadelphia (1992) discloses a general surgical procedure for attaching the Bosker Transmandibular Implant (TMI).) Note other embodiment described above may also be used. For example, the drill 1300 of FIG. 15a may be used with a ferrule inserted through the lower end of the outer segment 1320.

Figure 19A:
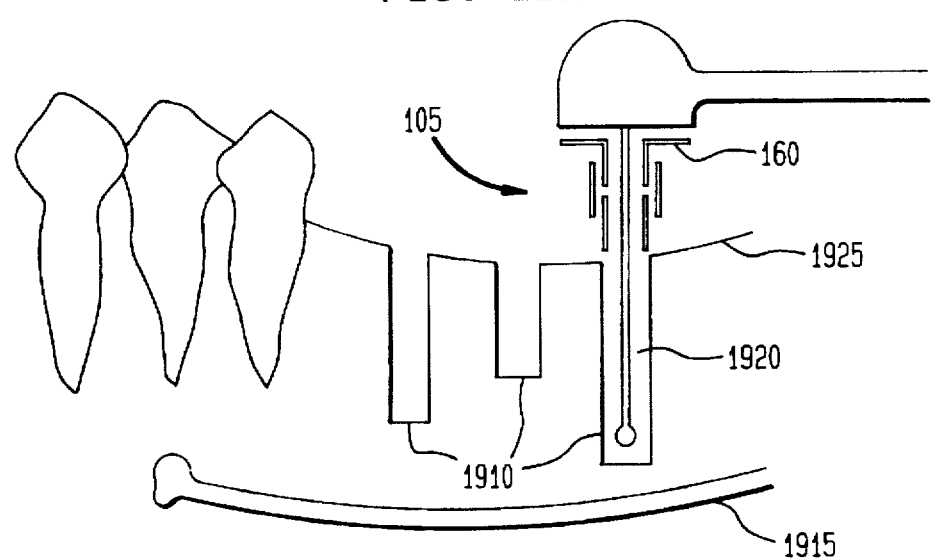
FIGS. 19a–19c illustrate the inventive drill guide of FIG. 4a in a dental root form implant application.

The drill guide 100 may be used for the placement of serial dental implants wherein a series of dental implant sites 1910 are drilled as shown in FIG. 19a. Each dental implant site 1910 is of varying depth and/or varying width. In the case of drilling series of holes of varying depth, without drilling too deep as to injure the mandibular nerve 1915, the same original drill bit 1920 may be used without changing the drill stop for drilling other sites. Instead, the length of the sleeve 105 is adjusted. For drilling a series of holes having varying widths, properly sized ferrule adapters 160 may be used.

After preparing the implant site 1910, the length of the sleeve 105 of the drill guide 100 is adjusted and a properly sized ferrule adaptor is inserted therein. Drilling is commenced after the sleeve 105 is placed on the cortical plates 1925 and the drill bit 1920 inserted through the ferrule adaptor 160. The adjustment of the length of the sleeve 105, placement of a proper ferrule adaptor 160 and drilling may be repeated until a desired size hole is achieved. For example, to widen a predrilled hole, the ferrule adapter 160 located in the sleeve 105 is exchanged with a properly sized ferrule adapter 160 which accepts a larger drill bit. Thereafter, the pre-drilled hole is widened using the larger drill bit inserted through the larger ferrule adaptor 160 located in the sleeve 105. Exchanging the ferrule adaptor 160 located in the sleeve 105 with a larger properly sized ferrule adaptor before drilling to widen the pre-drilled hole maintains the original center of the drill bit in the progressive steps of widening the hole.

Figure 19B:
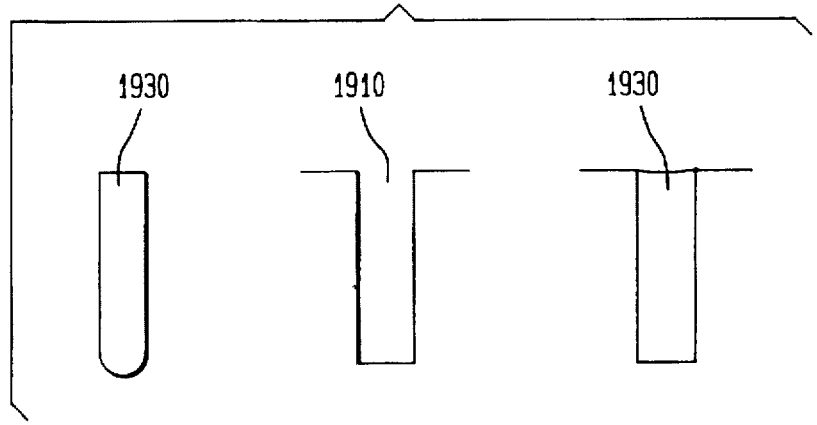
Figure 19C:
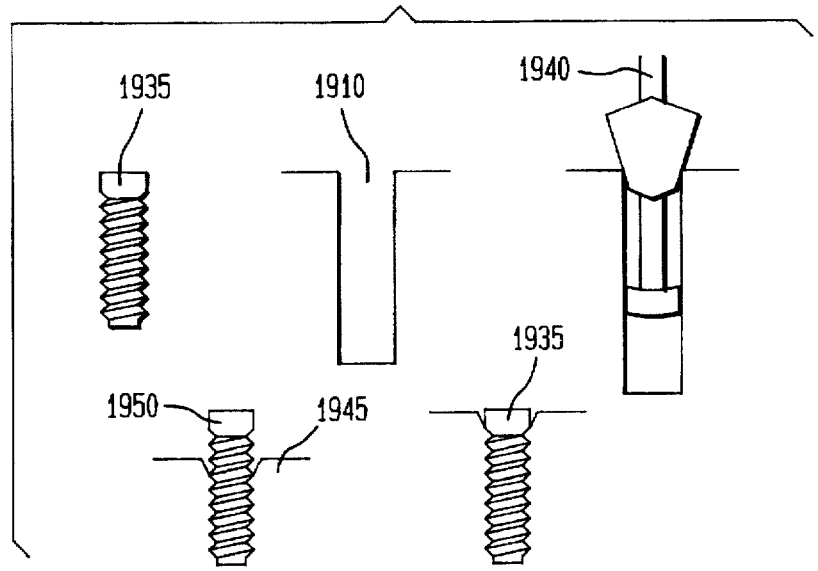

The implant could be either a press-fit endosseous cylindrical implant 1930 or a threaded implant 1935 as shown on FIGS. 19b–19c. FIG. 19c shows preparation of the implant site 1910 for implanting a screw type implant 1935. To maintain the original centering, the ferrule adapter 160 located in the sleeve 105 is again exchanged with a properly sized ferrule adapter 160 which accepts a counterbore 1940. The counterbore 1940 is used to enlarge the top portion 1945 of the implant site 1910. A screw tap 1950 is used to form threads in the hole 1950 and the threaded implant 1935 is screwed into the tapped implant site 1910. Alternatively, a self tapping implant may be screwed into the implant site 1910.

A similar method could be used for affixing a bone graft to a bone, using either positional or lag screws, wherein different size screws are used in a serial fashion. Instead of affixing a bone graft to a bone, two bone segments can be affixed together with lag screws. In such a case, it is often desirable to prepare one hole in the first bone segment, and an opposing different sized hole in the second bone segment. Such a procedure is shown in FIGS. 20a–20d and described in Greenberg, A M Ed. "Cranio-Maxillofacial Fractures: Principles of Internal Fixation Using the AO-ASIF Technique", Springer-Verlag, New York (1993).

As shown in FIGS. 20a–20d, a receptor site 2010 in a fractured mandibular bone 2020 is prepared for insertion of a lag screw 2030 as follows. After an incision is made, and the bones reduced to a correct anatomical position, the surgeon inserts into the incision a properly adjusted sleeve 105 having a properly sized ferrule adapter 160. Once the sleeve 105 contacts the bone, the surgeon commences drilling a gliding hole 2035 through in the near cortex 2040. Thereafter, the surgeon readjusts the length of the sleeve 105 and insert a smaller sized ferrule adapter into the sleeve 105. After centering the sleeve 105 over the gliding hole 2035, the surgeon drills a traction hole 2045 coaxially through the far cortex 2050. It is essential that the gliding and traction holes 2035, 2040 be drilled coaxially. To that effect, the smaller sized ferrule adapter ensures that the traction hole 2045 is centered about the gliding hole 2035 and drilled coaxially therethrough, along the same longitudinal axis 2055 of the gliding hole 2035. To further ensure alignment of the traction hole 2045 and the gliding hole 2035, the extension sleeve 250 of FIG. 5b (or 750 of FIG. 10b) may be modified so that its end 280 (780 of FIG. 10B) fits into the gliding hole 2035.

Figure 20A:
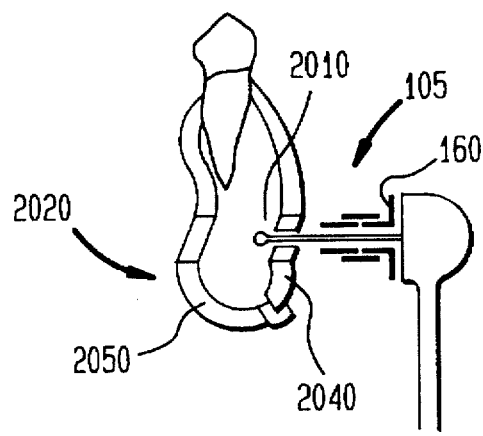
FIGS. 20a–20d illustrate the inventive drill guide of FIG. 4a in a affixing together segments of fractured bones.
Figure 20B:
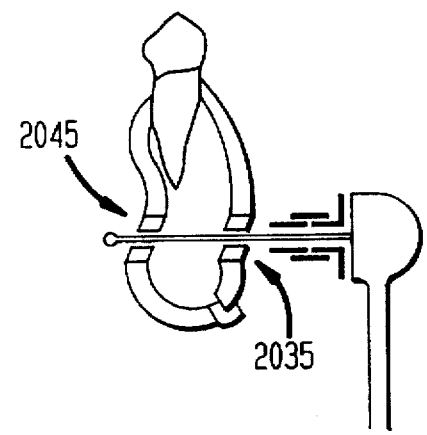
Figure 20C:
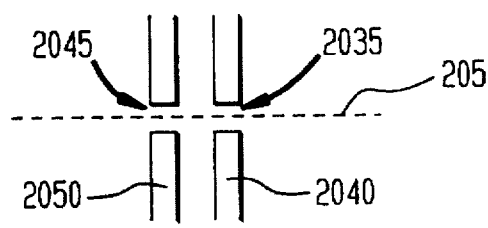
Figure 20D:
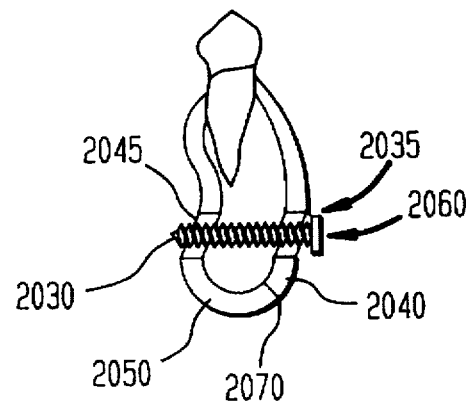

Similar to the procedure mentioned above in connection with the root form implant surgery, the inlet of the gliding hole is countersunk in the near cortex 2040 as shown in FIG. 20d. This is done by enlarging the inlet 2060 of the gliding hole 2035 using the countersink drill bit after the length of the sleeve 105 is properly adjusted and a correctly sized ferrule adapter inserted in the sleeve 105. Next, the traction hole 2045 is tapped using a screw tap and a lag screw 2030 is screwed into the traction hole 2045 through the gliding hole 2035. Insertion of the lag screw 2030 into the traction hole 2045 results in compression of the fracture 2070. Countersinking is important as it allows the compressing forces of the screw head generated from the lag screw to be distributed over a broader area. This prevents microfractures and shearing of the near cortex. Care must be taken to avoid countersinking beyond the cortical plate, as this will lessen the support of the screw.

The drill guide 100 ensures that the gliding and traction hole 2035, 2045 are drilled/countersunk to the proper depth and are coaxially centered along the same longitudinal axis. This is accomplished by using a ferrule adapter having an outer diameter equalling the diameter of the gliding hole 2035 and an inner diameter equalling the diameter of bit used to drill the traction hole 2045. This sized ferrule adapter is inserted into the sleeve 105. The end of this sized ferrule adapter protruding from the sleeve 105 is inserted into the gliding hole 2035 thus acting as a centering guide.

The drill guide 100 is also useful for affixing a prosthesis, such as a miniplate, where several different width holes must be drilled, or for drilling a hole and then widening the drilled hole with a larger width bit. In the technique of miniplate osteosynthesis, the incision is made in the region to which the miniplate 100 is to be secured. The bone fragments are reduced to their correct anatomical positions and a miniplate is positioned on the bone fragments. The drill guide 100 is then adjusted to a preselected length and positioned over the first hole of the miniplate. The lower opening may be chamfered or the chamfered extension sleeve may be attached to the lower opening so that it fits snugly into the countersunk holes of the miniplate. In this manner, the miniplate may be held in place by the drill guide while the hole is drilled. After the hole is drilled, a screw is inserted to secure the miniplate to the bone. This procedure may also be used for a mandibular staple implant or the Bosker Transmandibular Implant (TMI). The Bosker Transmandibular Implant may be modified so that multiple drill guides 100 can be used with the Bosker TMI.

When this entire procedure is completed for one hole, the operator moves to the next hole of the miniplate and repeats the procedure until the miniplate has been properly secured into position on the reduced bone structure. That is, the operator positions the drill guide over the next hole of the miniplate. The length of the sleeve 105 may be adjusted depending on the bone site and the desired length of the drill bit protruding from the sleeve 105. If necessary, the operator may replace the ferrule 160 with an appropriate width ferrule for drilling the next hole or inserting the screw therein.

Instead of a miniplate, a surgical guide template, for example used with the Bosker Transmandibular Implant (TMI), may be attached to the bone to be drilled. The surgical guide template is a customized template, specifically formed for each patient, having holes positioned at locations at which the surgeon is to drill into the bone. The surgical guide template may be attached to the bone in a similar fashion as the attachment of the miniplate. Alternatively, the surgical guide template may be held over the bone, for example, manually held by a hand or by screws. Thereafter, the surgeon systematically proceeds to drill holes into the bone at each location indicated by the surgical guide template as follows. The surgeon adjusts the sleeve 105 (FIG. 4a) of the drill guide 100 and places the appropriate ferrule 160 therein. The surgeon positions the drill guide 100 at the hole position of the surgical guide template and drills a hole. The surgeon then proceeds to the next hole.

Figure 21A:
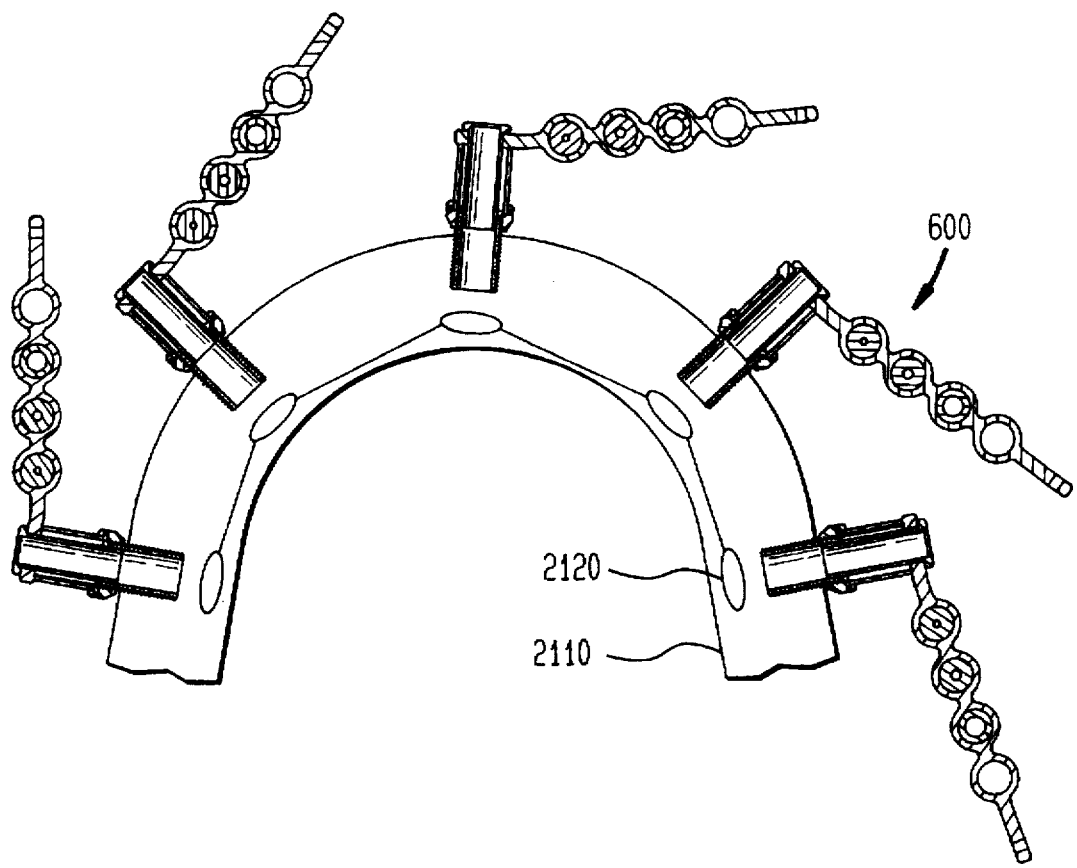
FIGS. 21a–21b show the inventive drill guide of FIG. 9 attached to a surgical guide template.

Multiple adjustable drill guides cannot be used with the Bosker TMI, since Bosker TMI uses a template with a preset drill guide. However, for a template having multiple holes, the inventive drill guide 100 may be attached to each hole resulting in a template having multiple attached drill guides 100. FIG. 21a shows a template 2110 with multiple holes 2120, where multiple drill guides 600 (of FIG. 9 or 100 of FIG. 4a) are attached to the template 2110. Such templates 2110 may be generated from a mold of the bone which the template is to be attached to. If making such a mold is not practical, then the template may be generated from a three dimensional model of the bone. For example, a computer assisted three dimensional scan of the bone is made or a three dimensional model of the bone is used to generate the template 2110. In addition, the template 2110 and the inventive drill guide 600 can be used in conjunction with computer assisted surgery.

Figure 21B:
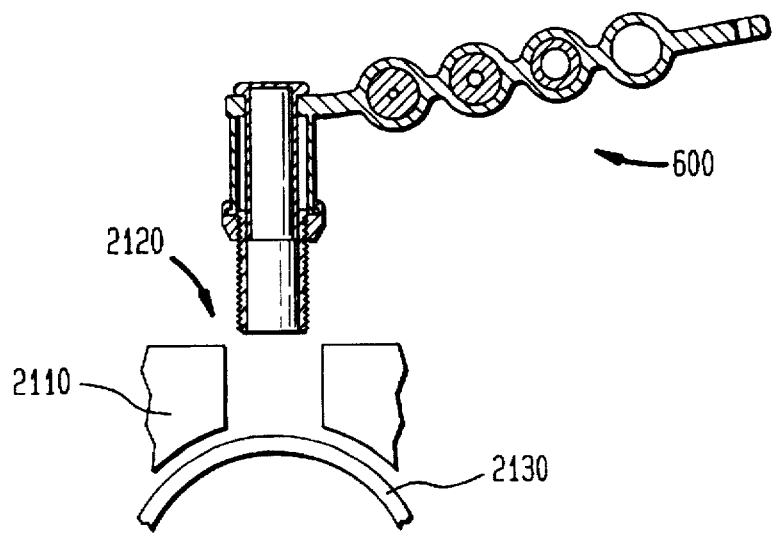

FIG. 21b shows a cross-section and a side view of the template 2110 attached to a bone 2130. A drill guide 600 is secured to the template 2110 covering the hole 2120. The drill guide 600 is used in conjunction with the template 2110 to drill a precise hole having a desired depth, width and orientation.

Figure 21C:
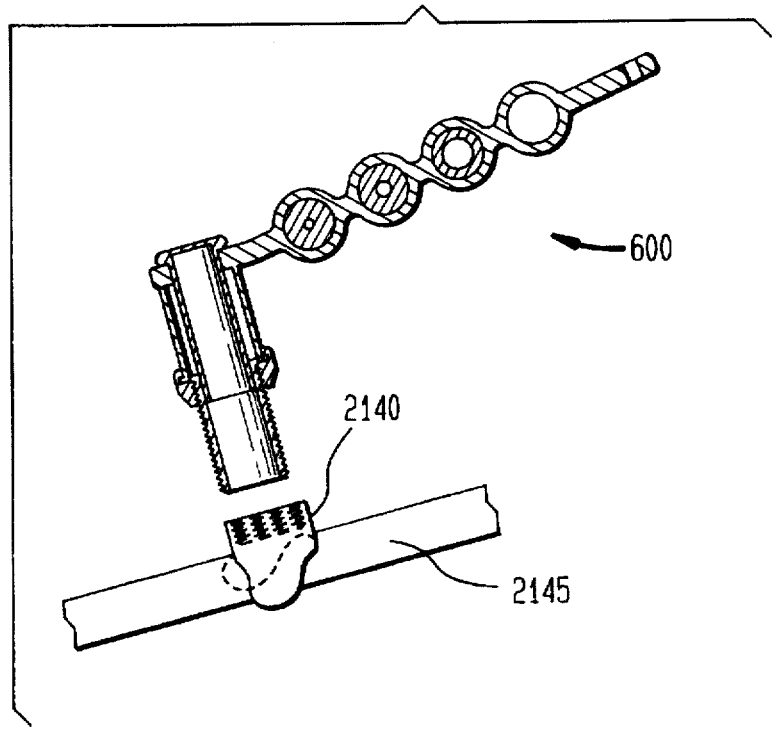
FIG. 21c shows the inventive drill guide with a contoured extension sleeve.

In another embodiment, shown in FIG. 21c, the drill guide 600 is used in conjunction with a contoured extension sleeve 2140. The contoured extension sleeve 2140 is shaped to fit on a bone 2145 or other non-flat shaped material. The contoured extension sleeve 2140 is placed on or attached to the bone 2145 and provides for a more stable and precise drilling. For example, for drilling bones of various shapes, different sized and contoured extension sleeves 2140 are provided. Using the contoured extension sleeve 2140 greatly facilitates drilling precise holes in bones.

Figure 21D:
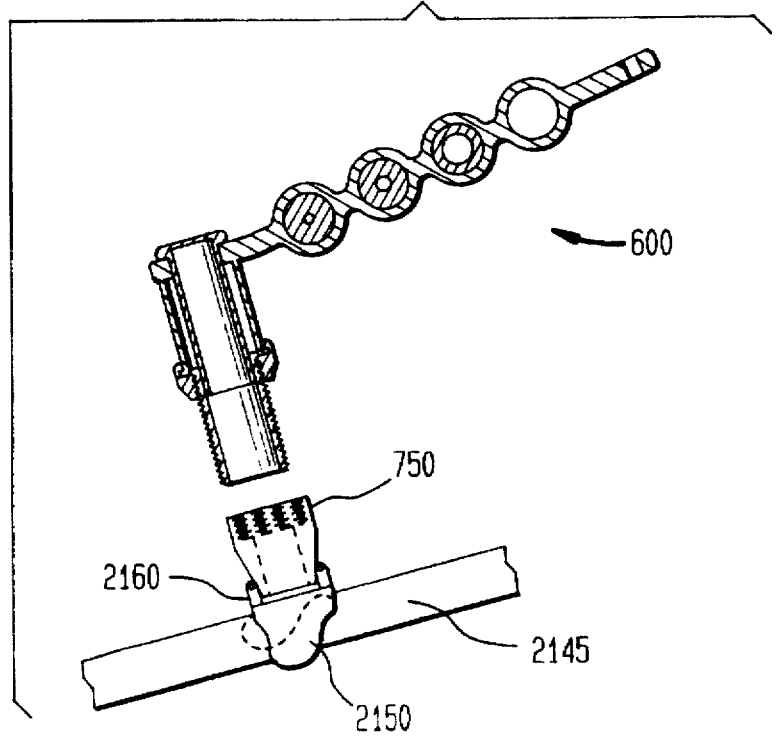
FIGS. 21d–21f show the inventive drill guide with a base plate.

FIG. 21d shows an alternate embodiment where a foot or base plate 2150 is contoured to fit on the bone or other material to be drilled. The base plate 2150 is attached via hinges 2160 to the extension sleeve 750 of FIG. 10b (or extension sleeve 250 of FIG. 5b for using the drill guide 100). Thereafter, the drill guide 600 can be attached to the extension sleeve 750 and used in the same manner describe above. The orientation or angle of the drill guide 600 may be changed by using the hinges 2160 or ball joints (not shown) to attach the extension sleeve 750 to the base plate 2150. Using hinges allows orienting the drill guide 600 in two dimensions, whereas ball joints allow a three dimensional orientation.

Figure 21E:
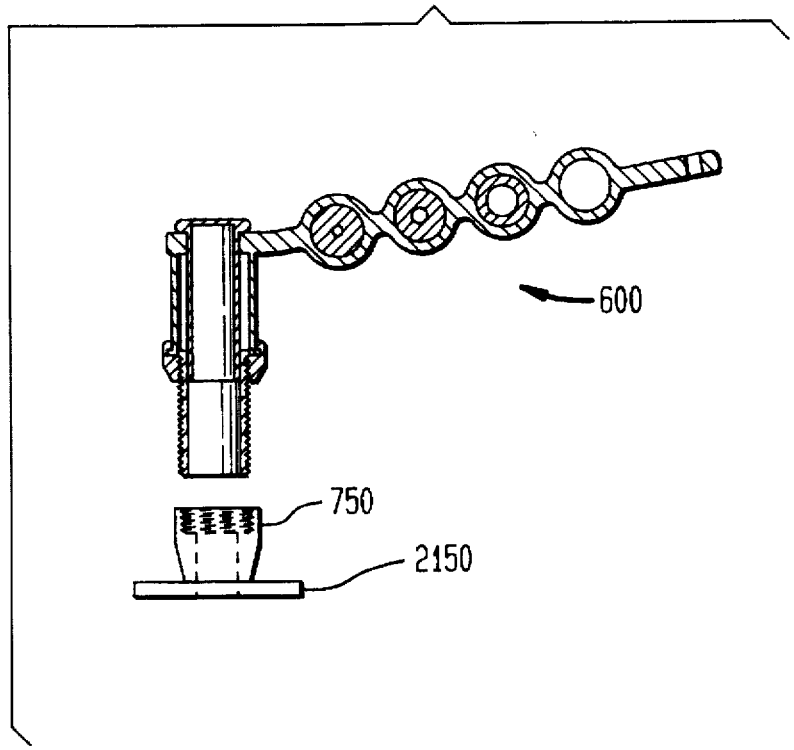
Figure 21F:
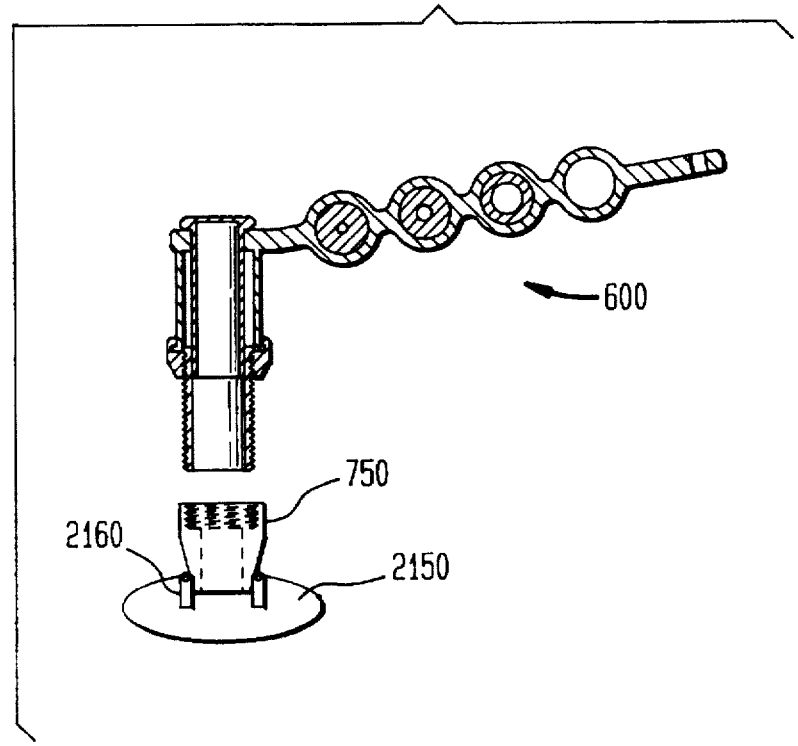

The base plate 2150 may have any shape. For example, the base plate 2150 may have a flat surface or a surface contoured to fit on a particular shaped material to be drilled, or a surface contoured to fit on the template 2110. In FIG. 21d, the base plate 2150 is curved to securely fit on the bone 2145. FIG. 21e-f show a base plate 2150 having a flat surface. The base plate 2150 is permanently attached to the extension sleeve 750 in FIG. 21e. In FIG. 21f, the base plate 2150 is attached to the extension sleeve 750 via hinges 2160. Alternatively, the base plate 2150 may have a surface that mates with the template 2110 and may be attached to the template 2110 over the hole 2120 (FIG. 21a). To change the orientation or angle of drilling, the drill guide 600 is moved about the hinges 2160. Instead of being attached to the extension sleeve 750, the base plate 2150 may be directly attached (via the hinges 2160) to the drill guide 600. It is noteworthy that using the drill guide 600 in conjunction with templates is not confined to medical applications. Templates with attached drill guides 600 may be used in industrial, commercial or consumer applications, in a similar manner described above.

Figure 22:
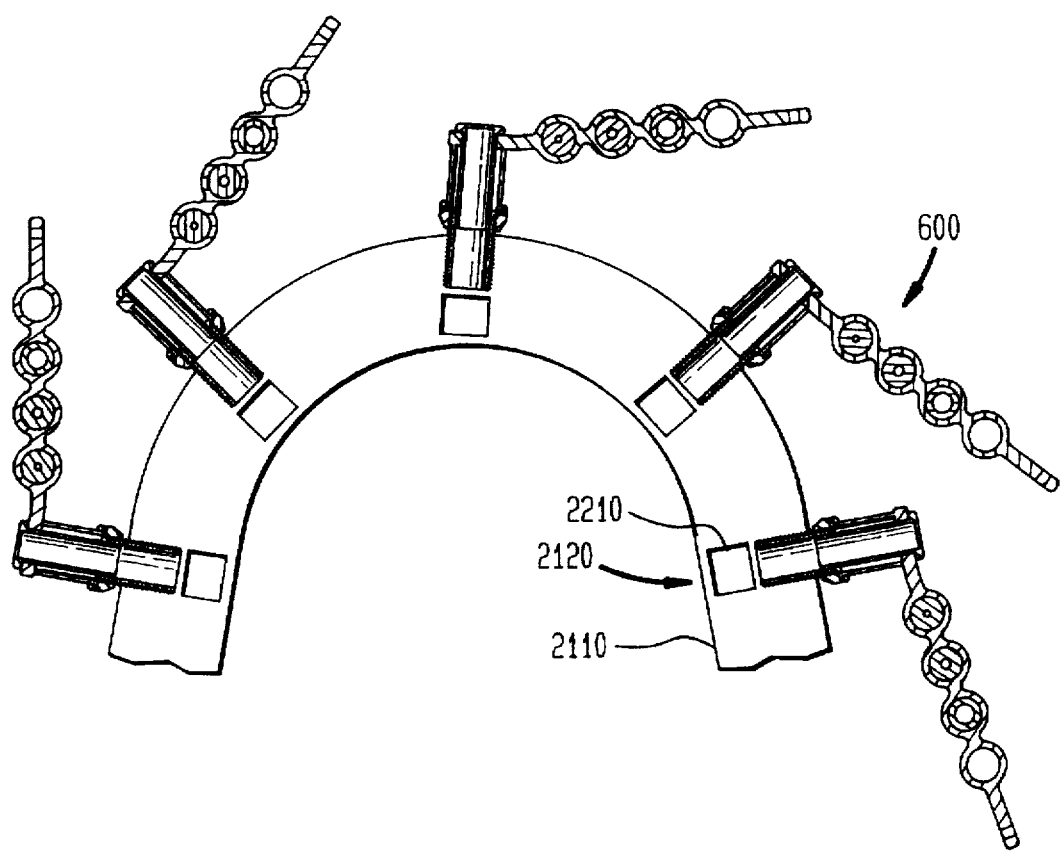
FIG. 22 shows the inventive drill guide of FIG. 9 positioned over a tube of a surgical guide template.

FIG. 22 shows the template 2110 of FIG. 21a with tubes 2210 attached to the holes 2120. The tubes 2210 are attached at a preset angle, therefore, the tubes 2210 guide the drill bits and allow drilling at the preset angle. Such tubes 2210 are manufactured by NobelPharma of Chicago, Ill. and may be used in conjunction with the surgical template 2110, for example, in knee prosthesis. For better control over the drilled holes, drill guides 600 of FIG. 9 (or 100 of FIG. 4a) are held over the tubes 2210. In addition to drilling holes at the preset angle, the use of the inventive drill guide 600 attached to the tubes 2210 allows drilling holes of different depths and widths. Furthermore, predrilled holes can be widened without offsetting the center of the predrilled holes by drilled about a coaxially centered axis (as explained in connection with FIGS. 20a–20d).

Figure 23:
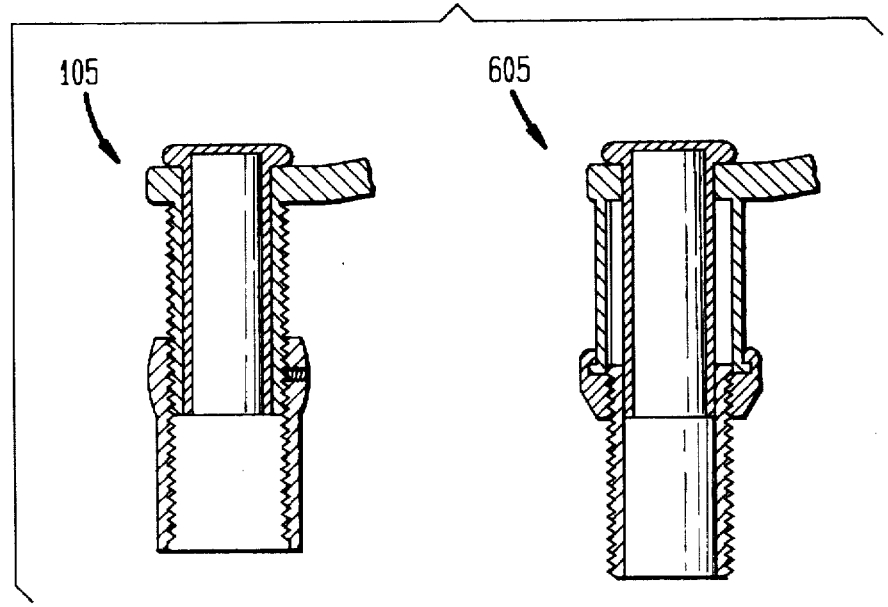
FIG. 23 illustrates a cross-sectional view of an embodiment of the drill guide without a handle.

FIG. 23 shows another embodiment of the inventive drill guide that does not have a handle. In this embodiment, the adjustable sleeve 605 of FIG. 9 (or 105 of FIG. 4a) and a properly sized ferrule 160 are used to adjust the depth and width of a drilled hole. Such an embodiment is desirable when attaching multiple adjustable sleeve 105 to a template such as the template 2110 of FIGS. 21a and 23. The adjustable sleeve 105 may be directly attached to the template 2110 over the hole 2120, or attached to the tube 2210 covering the hole 2120. Using this embodiment, without the handle, reduces clutter and provides more space to work, especially for small templates. Using the adjustable sleeve 105 maintains the benefit of being able to adjust the depth and width of a drilled hole, and to widen a predrilled hole along its center.

Figure 24A:
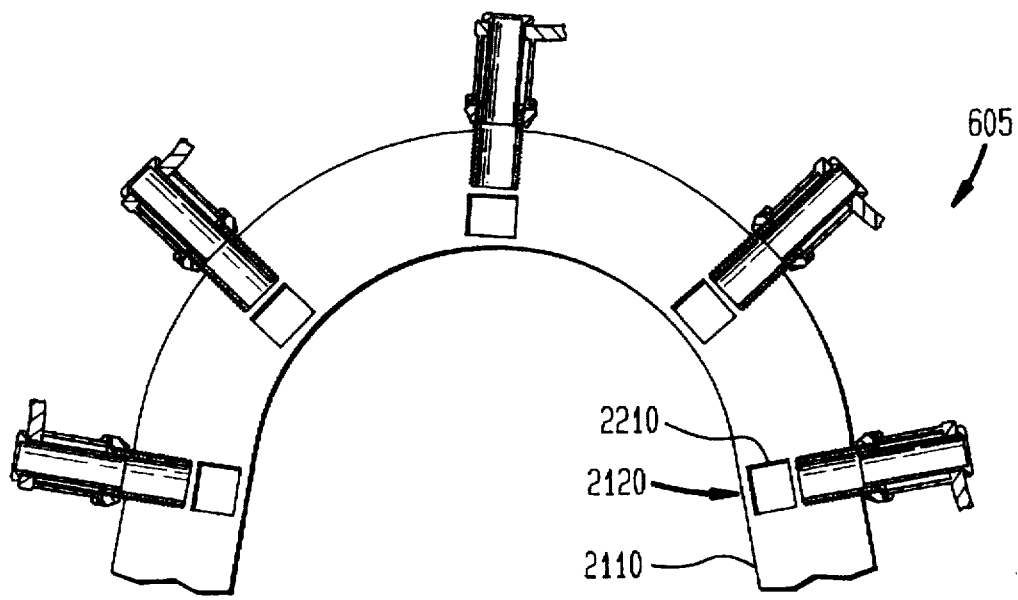
FIGS. 24a–b show the inventive drill guide of FIG. 23 positioned over or attached to the tube of the surgical guide template shown in FIG. 22.
Figure 24B:
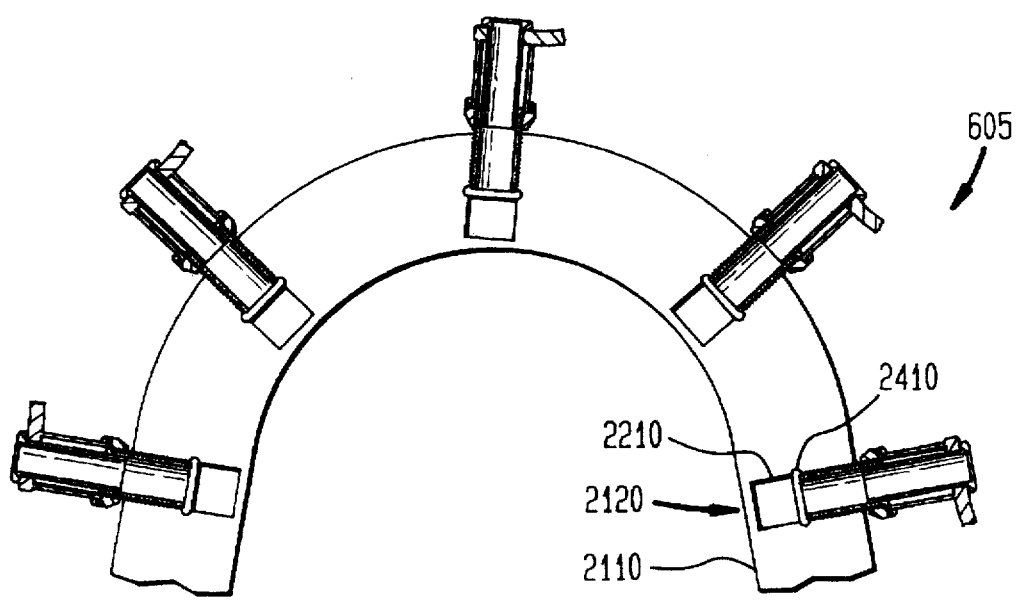

The embodiment shown in FIG. 23, i.e., the adjustable sleeve 605 (without a handle) is particularly suited for use in conjunction with the template 2110 having the tubes 2210 shown in FIG. 22. FIG. 24a shows the adjustable sleeves 605 positioned over the tubes 2210. Alternatively, to alleviate the need to hold the adjustable sleeve 605 over the tube 2210, the adjustable sleeve 605 may be attached to the tube 2210 as shown in FIG. 24b. Illustratively, a ball joint 2410 is used to attach the adjustable sleeve 605 to the tube 2210. Attaching the tube 2210 to the template 2110 fixes the angle of entry of the drill bit and the location of the hole to be drilled (i.e., the point of entry of the drill bit). However, the depth and width of the hole cannot be properly varied. Furthermore, to widen predrilled holes, there are no provisions for accurately guiding the drill bit centrally to the predrilled hole.

Attaching the adjustable sleeve 605 to the tube 2210 provides the ability to control the depth and width of drilling. In addition, for widening a predrilled hole, the adjustable sleeve 605 provides coaxial alignment of the drill bit with the axis of the predrilled hole. Thus, the adjustable sleeve 605 allows proper widening of a predrilled hole by accurately centering and guiding the drill bit.

Figure 25:
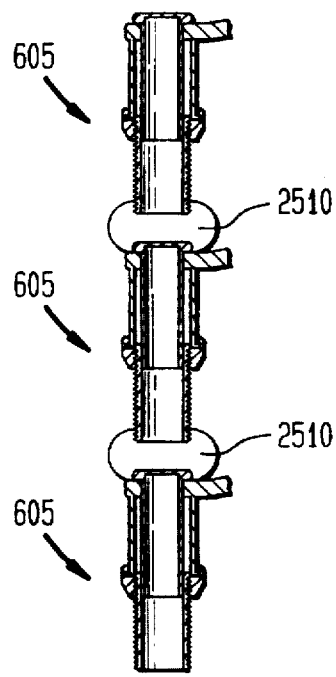
FIG. 25 shows a series connected sequence of the embodiment shown in FIG. 23.

FIG. 25 shows a sequence of multiple adjustable sleeves 605 connected in series. The adjustable sleeve 605 may be connected by a ball joint, a hinge, or a shell of acrylic 2510. Similar to the single adjustable sleeves 605 of FIG. 23, this sequence of multiple adjustable sleeves 605 may be directly attached to the template 2110 or attached to the tube 2210.

Figure 26:
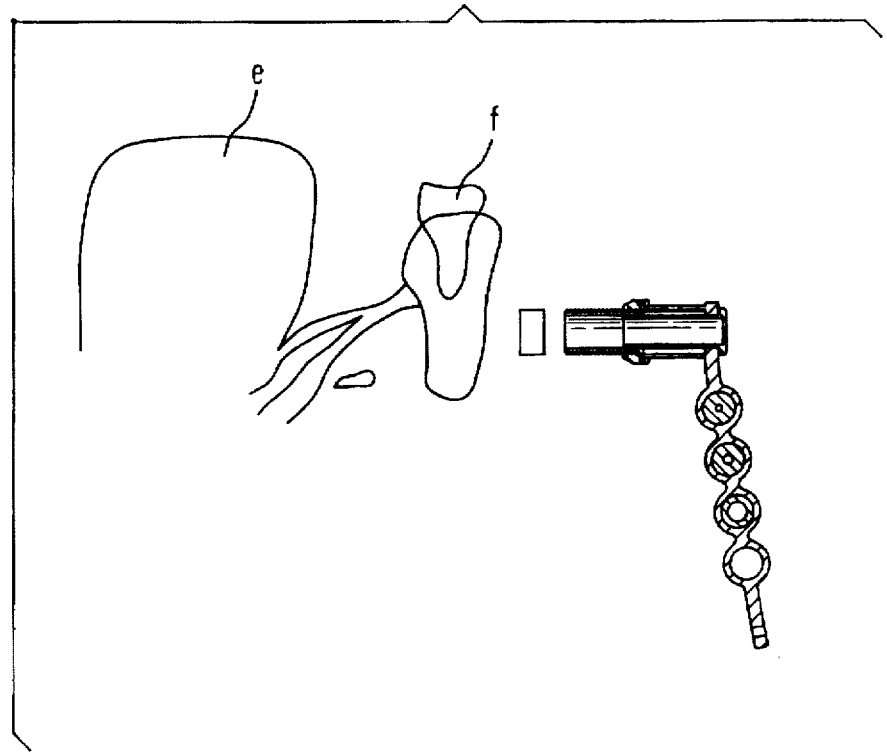
FIG. 26 illustrates the inventive drill guide of FIG. 9 in a mandibular application.
Figure 27:
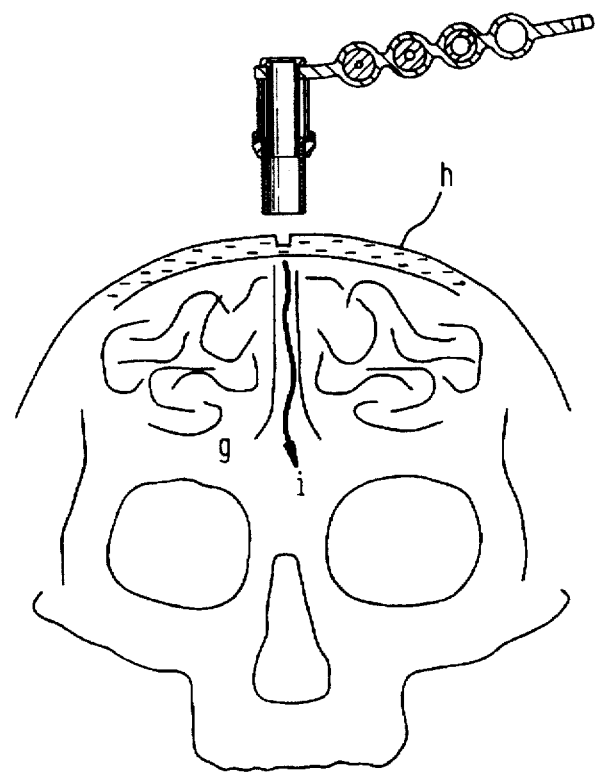
FIG. 27 illustrates the inventive drill guide of FIG. 9 in a cranial application.

The drill guide 600 (FIG. 9) may also be used in mandibular and cranial regions and such applications are illustrated in FIGS. 26 and 27 respectively. In FIG. 26, f designates the mandible in the coronal region with the tongue being shown as e. In FIG. 27, g designates the brain within the cranium h. The label i designates a hole drilled using the device which does not penetrate entirely through the cranium h to the inner cortex. The drill guide 100 is particularly suited for application in which it is desired to drill into the cranium h no deeper than within 5 mm of the inner side of the cranium h.

It will be apparent to those skilled in the art that the inventive drill guide and drill can also be used for wire fixation in addition to rigid internal fixation with a bone plate.

Consumer/Industrial Applications

Figure 28:
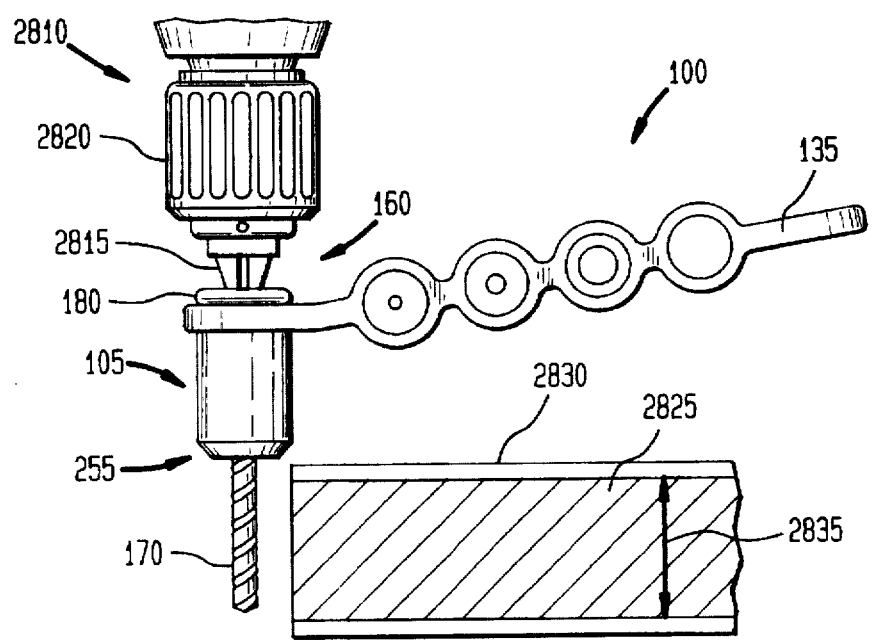
FIG. 28 illustrates the inventive drill guide of FIG. 9 in an application with a hand held consumer or industrial drilling tool.

FIG. 28 illustrates the inventive drill guide 100 of FIG. 4a (or 600 of FIG. 9) in an application with a hand held consumer or industrial drilling tool 2810. A drill bit 170 is inserted into, and secured by, the jaws 2815 of the drill chuck 2820. A properly sized ferrule adapter 160 is removed from one of the storage compartments 145 of the handle 135. The ferrule adapter 160 is inserted into the adjustable sleeve 105. The lip 180 of the inserted ferrule adapter 160 drill guide 100 rests on the periphery of the adjustable sleeve 105. The length of the sleeve 105 is adjusted as previously explained. To verify the correct length of the sleeve 105, the drill bit 180 is inserted into the sleeve 105 until the quick coupling 2815 abuts the lip 180 of the ferrule adapter 160. The portion of the drill bit protruding from the lower opening 255 of the sleeve 105 is placed against a ruler to verify its length. Accordingly, the length of the sleeve 105 is adjusted.

Alternatively, or in addition, the protruding bit length can be verified by positioning it adjacent the material 2825 to be drilled. Illustratively, the material 2825 is wood, plastic, cement, metal, etc. The lower opening 255 of the sleeve 105 is placed abutting the upper surface 2830 the material 2825. The protruding portion of the drill bit 170 is compared (by eye) to the thickness 2835 of the material 2825 to verify the desired depth of the hole to be drilled. The length of the sleeve 105 is adjusted to achieve a desired length of the protruding portion of the drill bit 170. Thereafter, the lower opening 255 of the sleeve 105 is placed on the upper surface 2830 of material 2825 at the location to be drilled and a hole is drilled. The jaws 2815 abut the lip 180 of the ferrule 160 to produce a hole with the desired depth. The drill guide 100 acts as a stop, preventing the drilling of holes deeper than the length of the portion of the drill bit 170 protruding from the lower opening 255 of the sleeve 105.

This process is repeated to drill as many holes of the same depth and width as desired or to widen pre-drilled holes. To enlarge the width of a pre-drilled hole or drill a new wider hole, a wider sized ferrule adapter 160 is inserted into the sleeve 105 and a wider drill bit 170 used. Different depth holes can be drilled by simply adjusting the length of the sleeve 105.

In summary, a drill guide has been described with removable ferrules having different width bores. The ferrule having the appropriate width is inserted into the sleeve of the drill guide. The drill guide thus simplifies precision drilling and surgical procedures wherein many different width instruments are necessary or where the appropriate width instrument is not known prior to the surgery.

While the invention has been described by the reference to specific embodiments, this was for purposes of illustration only and should not be construed to limit the spirit or the scope of the invention.

The claimed invention is:

1. A drill guide comprising:

a handle, and a sleeve having a first end attached to one end of said handle, said sleeve comprising:

a first bore, a first ferrule dimensioned for demountable insertion into one end of said sleeve and having a second bore dimensioned to receive therethrough an instrument having a particular width, and a second ferrule which is demountably attached to an end of said first ferrule, said second ferrule extending from an end opposite said one end of said first bore, wherein said exposed end of said second ferrule has markings on an outer surface thereof indicating a penetration depth of said instrument inserted through said second bores of the attached pair of ferrules.

2. A drill guide comprising:

a handle, and a sleeve having a first end attached to one end of said handle, said sleeve comprising:

a first bore, a first ferrule dimensioned for demountable insertion into one end of said sleeve and having a second bore dimensioned to receive therethrough an instrument having a particular width, and a second ferrule which is demountably attached to an end of said first ferrule, said second ferrule extending from an end opposite said one end of said first bore, wherein said exposed end of said second ferrule has a longitudinal slot for viewing said instrument inserted through said second bores of the attached pair of ferrules.

3. A drill guide comprising:

a handle, a sleeve having a first end attached to one end of said handle, said sleeve comprising:

a first bore, a ferrule dimensioned for demountable insertion into one end of said sleeve and having a second bore dimensioned to receive therethrough an instrument having a particular width, and an extension sleeve attached to a second end of said sleeve.

4. The drill guide of claim 3 wherein said extension sleeve has one end shaped to fit on a material to be drilled, and has hinges attached to a second end of said extension sleeve, said second end being located opposite said first end, wherein said hinges are for hingedly attaching said extension sleeve to said second end of said sleeve.

5. The drill guide of claim 4 wherein said one end of said extension sleeve is curved to fit on a cylindrical body.

6. A drill guide comprising:

a handle, a sleeve having a first end attached to one end of said handle, said sleeve comprising:

a first bore, a ferrule dimensioned for demountable insertion into one end of said sleeve and having a second bore dimensioned to receive therethrough an instrument having a particular width, and a base plate having one surface shaped to fit on a material to be drilled, and having hinges attached to a second surface located opposite said one surface, wherein said base plate is hingedly attached to a second end of said sleeve.

7. A drill guide comprising:

a handle having a plurality of compartments for storing a plurality of ferrules, wherein each of said compartments has an opening on one end for receiving one of said ferrules, and another end having a snap-on device for retaining said one ferrule within said compartment, and a sleeve having a first end attached to one end of said handle, said sleeve comprising:

a first bore, a ferrule dimensioned for demountable insertion into one end of said sleeve and having a second bore dimensioned to receive therethrough an instrument having a particular width.

8. A drill guide comprising:

a handle, and a sleeve having a first end attached to one end of said handle, and an inner segment with a third bore and an outer segment with a fourth bore, wherein said inner segment is adjustably mounted within said fourth bore of said outer segment, said third and fourth bores being axially aligned to form said first bore and wherein said inner segment is adjustably retractable into, and extendable from, one end of said fourth bore of said outer segment to change an overall length of said sleeve, and is fixedly attached to said handle and has an outer threaded surface, and wherein said outer segment has an inner threaded surface and is rotated about said inner segment so as to change a length of said sleeve, said sleeve comprising:

a first bore, a ferrule dimensioned for demountable insertion into one end of said sleeve and having a second bore dimensioned to receive therethrough an instrument having a particular width.

9. The drill guide of claim 8 wherein a top end of said outer segment is shaped into a knurled grip.

10. The drill guide of claim 9 further comprising an insert within said knurled grip for preventing thread slippage.

11. The drill guide of claim 8 further comprising an extension sleeve having an extension bore extending therethrough, a top portion of said extension sleeve having a threaded outer surface for screwing into said outer segment.

12. The drill guide of claim 11 wherein said extension sleeve has a tapered lower portion.

13. A drill guide comprising:

a handle, a sleeve having a first end attached to one end of said handle, an inner segment with a third bore, and an outer segment with a fourth bore, wherein said inner segment is adjustably mounted within said fourth bore of said outer segment, said third and fourth bores being axially aligned to form said first bore and wherein said inner segment is adjustably retractable into, and extendable from, one end of said fourth bore of said outer segment to change an overall length of said sleeve, said sleeve comprising:

a first bore, a ferrule dimensioned for demountable insertion into one end of said sleeve and having a second bore dimensioned to receive therethrough an instrument having a particular width, and a depth adjusting nut, rotatably attached to a lower end of said outer segment, wherein said outer segment is fixedly attached to said handle and has an inner threaded surface, and wherein said inner segment has an outer threaded surface and is screwed into said depth adjusting nut to form said bore of said sleeve, said depth adjusting nut being turned so as to change a length of said sleeve.

14. The drill guide of claim 13 wherein an inner surface of said outer segment has a key and said outer threaded surface of said inner segment has a keyway in which said key slides.

15. The drill guide of claim 14 further comprising an extension sleeve having an extension bore extending therethrough, a top portion of said extension sleeve having a threaded inner surface for screwing over said outer segment.

16. A drill guide comprising:

a handle, and a sleeve having a first end attached to one end of said handle, said sleeve comprising:

a first bore, a ferrule dimensioned for demountable insertion into one end of said sleeve, having a second bore dimensioned to receive therethrough an instrument having a particular width, and having teeth on an outer surface thereof, a rod slidably attached to said handle having a tip extending into said sleeve, a spring for biasing said tip to engage said teeth so as to hold said ferrule at a desired insertion within said first bore of said sleeve, and a lever attached to said rod for disengaging said tip from said teeth, when said lever is urged against said bias of said spring, for permitting adjustment of said insertion of said inner segment within said first bore.

17. A drill guide comprising:

a handle, a sleeve having a first end attached to one end of said handle, said sleeve comprising:

a first bore, a first ferrule dimensioned for demountable insertion into one end of said sleeve and having a second bore dimensioned to receive therethrough an instrument having a particular width, and a ferrule extractor having a crown and a grip attached to said crown, wherein said crown is dimensioned to slide onto a lip located around an end of said ferrule, so that pulling said grip extracts said ferrule.

18. The drill guide of claim 17 wherein said grip is round.

19. The drill guide of claim 18 wherein said grip is straight having an end dimensioned to slide onto said handle of said drill guide.

20. A drill guide comprising:

a sleeve having a first end, said sleeve comprising:

a first bore, and a ferrule dimensioned for demountable insertion into one end of said sleeve and having a second bore dimensioned to receive therethrough an instrument having a particular width, additional sleeves connected in series, wherein said additional sleeves are identical to said sleeve, and connecting elements interconnecting in series said additional sleeves and connecting said sleeve in series to said series interconnected additional sleeves.

* * * * *

UNITED STATES PATENT AND TRADEMARK OFFICE
CERTIFICATE OF CORRECTION

PATENT NO.    : 5,743,916
DATED         : April 28, 1998
INVENTOR(S)   : Greenberg et al.

It is certified that error appears in the above-identified patent and that said Letters Patent is hereby corrected as shown below:

Title page,
Item [73], Assignee, should read -- Human Factors Industrial Design, Inc., New York, NY & Greenberg Surgical Technologies, LLC, New York, NY. --;

Signed and Sealed this

Twenty-first Day of October, 2003

JAMES E. ROGAN
*Director of the United States Patent and Trademark Office*